US011655298B2

(12) United States Patent
Hasegawa et al.

(10) Patent No.: US 11,655,298 B2
(45) Date of Patent: May 23, 2023

(54) COMPOSITION FOR TREATING FULMINANT ACUTE PNEUMONIA INCLUDING CD69 ANTAGONIST

(71) Applicants: YAMAGUCHI UNIVERSITY, Yamaguchi (JP); NATIONAL UNIVERSITY CORPORATION CHIBA UNIVERSITY, Chiba (JP)

(72) Inventors: Akihiro Hasegawa, Yamaguchi (JP); Hidetaka Ogino, Yamaguchi (JP); Toshinori Nakayama, Chiba (JP)

(73) Assignees: YAMAGUCHI UNIVERSITY, Yamaguchi (JP); NATIONAL UNIVERSITY CORPORATION CHIBA UNIVERSITY, Chiba (JP)

( * ) Notice: Subject to any disclaimer, the term of this patent is extended or adjusted under 35 U.S.C. 154(b) by 170 days.

(21) Appl. No.: 16/342,992

(22) PCT Filed: Oct. 20, 2017

(86) PCT No.: PCT/JP2017/038091
§ 371 (c)(1),
(2) Date: Sep. 13, 2019

(87) PCT Pub. No.: WO2018/074610
PCT Pub. Date: Apr. 26, 2018

(65) Prior Publication Data
US 2020/0055940 A1    Feb. 20, 2020

(30) Foreign Application Priority Data

Oct. 21, 2016 (JP) ............................ JP2016-207046

(51) Int. Cl.
*C07K 16/28* (2006.01)
*A61P 11/00* (2006.01)

(52) U.S. Cl.
CPC .......... *C07K 16/2851* (2013.01); *A61P 11/00* (2018.01); *C07K 2317/76* (2013.01)

(58) Field of Classification Search
USPC ........................................................ 506/10
See application file for complete search history.

(56) References Cited

U.S. PATENT DOCUMENTS

| 2012/0121503 A1* | 5/2012 | Nakayama | ......... C07K 16/2896 424/1.49 |
| 2015/0118237 A1 | 4/2015 | Kojoh et al. | |
| 2016/0102139 A1 | 4/2016 | Nakayama et al. | |

FOREIGN PATENT DOCUMENTS

| JP | 2015074605 A | 4/2015 | |
| WO | 2013161814 A1 | 10/2013 | |
| WO | WO-2013161814 A1 * | 10/2013 | ............... A61P 29/00 |

OTHER PUBLICATIONS

Aoyagi et al. International Immunology vol. 23, No. 2, pp. 97-108, 2010. (Year: 2010).*
Reid et al. Modern Parasitology vol. 24, pp. 1612-1619, 2011 (Year: 2011).*
Llewellyn-Jones et al. Eur. Respir. J. No 8. pp. 1479-1487, 1995. (Year: 1995).*
Guidelines for the Management of Adults with Community-acquired Pneumonia Diagnosis, Assessment of Severity, Antimicrobial Therapy, and Prevention (Year: 2001).*
Reid et al., "Tumor-infiltrating neutrophils in pancreatic neoplasia," Modern Pathology, vol. 24, 2011, pp. 1612-1619.
Aoyagi et al., "Activation of pulmonary invariant NKT cells leads to exacerbation of acute lung injury caused by LPS through local production of IFN-γ and TNF-α by Gr-1+ monocytes," International Immunology, vol. 23, No. 2, 2010, pp. 97-108.
"Purified anti-mouse CD69 Antibody," Biolegend, Version 3, 2016.
Hayashizaki et al., "Myosin light chains 9 and 12 are functional ligands for CD69 that regulate airway inflammation," Science Immunology, 1, eaaf9154, 2016, pp. 1-10.
Yokoyama et al., "Characterization of a cell surface-expressed disulfide-linked dimer involved in murine T cell activation," The Journal of Immunology, vol. 141, 1988, pp. 369-376, http://www.jimmunol.org/content/141/2/369.
Sobel et al., "Aberrant expression of the very early activation antigen on MRL/Mp-lpr/lpr lymphocytes," The Journal of Immunology, vol. 150, 1993, pp. 673-682, http://wwwjimmunol.org/content/150/2/673.
Karlhofer et al., "Stimulation of murine natural killer (NK) cells by a monoclonal antibody specific for the NK1.1 antigen, IL-2-activated NK cells possess additional specific stimulation pathways," The Journal of Immunology, vol. 146, 1991, pp. 3662-3673, http://www.jimmunol.org/content/146/10/3662.
Shinoda et al., "Type II membrane protein CD69 regulates the formation of resting T-helper memory," PNAS, vol. 109, No. 19, 2012, pp. 7409-7414, www.pnas.org/cgi/doi/10.107/pnas.1118539109.

(Continued)

*Primary Examiner* — Gary B Nickol
*Assistant Examiner* — Khatol S Shahnan Shah
(74) *Attorney, Agent, or Firm* — Kilyk & Bowersox, P.L.L.C.

(57) ABSTRACT

It is an object to provide effective means for preventing and/or treating fulminant acute pneumonia. Provided are a pharmaceutical agent or pharmaceutical composition to be used for preventing and/or treating fulminant acute pneumonia, containing a CD69 antagonist, such as an antibody that specifically recognizes CD69 (anti-CD69 antibody), an agent for suppressing intra-alveolar neutrophil aggregation, containing a CD69 antagonist, such as an antibody that specifically recognizes CD69 (anti-CD69 antibody), an agent for suppressing pulmonary neutrophil infiltration, containing a CD69 antagonist, such as an antibody that specifically recognizes CD69 (anti-CD69 antibody), and a method of preventing and/or treating fulminant acute pneumonia, including administering a CD69 antagonist, such as an antibody that specifically recognizes CD69 (anti-CD69 antibody).

6 Claims, 13 Drawing Sheets

(56) References Cited

OTHER PUBLICATIONS

International Search Report and Written Opinion issued in corresponding International Patent Application No. PCT/JP2017/038091 (with English translation) dated Dec. 12, 2017 (15 pages).
International Preliminary Report on Patentability issued in corresponding International Patent Application No. PCT/JP2017/038091 (with English translation) dated Apr. 23, 2019 (12 pages).

* cited by examiner

Control mAb

| No treatment | treatment |
|---|---|
|  |  |

Anti-CD69 mAb

| No treatment | treatment |
|---|---|
|  |  |

COMPOSITION FOR TREATING FULMINANT ACUTE PNEUMONIA INCLUDING CD69 ANTAGONIST

TECHNICAL FIELD

The present invention relates to a composition containing a CD69 antagonist, which is a pharmaceutical agent or pharmaceutical composition for use in preventing and/or treating fulminant acute pneumonia. The present invention also relates to an agent for suppressing intra-alveolar neutrophil aggregation containing a CD69 antagonist. The present invention also relates to an agent for suppressing pulmonary neutrophil infiltration containing a CD69 antagonist. The present invention also relates to a preventive agent and/or therapeutic agent for fulminant acute pneumonia containing a CD69 antagonist. The present invention also relates to a method of preventing and/or treating fulminant acute pneumonia comprising administering a CD69 antagonist.

The present application is a National Stage Application of PCT/JP2017/038091, filed Oct. 20, 2017, which claims priority from Japanese Patent Application No. 2016-207046, which is incorporated herein by reference.

BACKGROUND ART

Fulminant acute pneumonia refers to a respiratory distress syndrome showing more severe symptoms as compared to acute respiratory distress syndrome (hereinafter sometimes abbreviated as ARDS). Acute pneumonia generally involves rapid occurrence of symptoms and rapid exacerbation of the symptoms, followed, after a short period of symptom improvement, by rapid healing. Meanwhile, fulminant acute pneumonia involves rapid occurrence of symptoms and rapid progression of pneumonia, and has a poor prognosis, that is, is liable to become severe, and also has a high risk of death.

ARDS is noncardiogenic pulmonary edema due to non-specific inflammation in an alveolar region triggered to be developed by some invasion into the body, and is characterized by severe hypoxemia and a reduction in lung compliance. ARDS is also characterized by a pathological image exhibiting intense neutrophil infiltration and diffuse alveolar damage (DAD). A period from the invasion to the development is generally several days or less, and a mortality rate after the development is more than 40%. ARDS is a disease that is considered a serious problem in clinical settings for, for example, the reason that ARDS is developed in about 20% of patients receiving artificial respiration in an intensive care unit and the like. Along with the development of ARDS, pulmonary capillary endothelial cells and alveolar epithelial cells are damaged. As a result, pulmonary edema and fibrosis are induced, leading to death by dyspnea. At present, treatment of ARDS has been attempted through mechanical ventilation and also through drug therapy with a steroid, a neutrophil elastase inhibitor, or the like, which has been unable to serve as an effective treatment method. In addition, previous studies have reported, for example, involvement of lipid mediators and cytokines, such as interferon-γ (IFNγ), produced by infiltrating activated neutrophils in the development of ARDS, but a detailed development mechanism thereof has yet to be elucidated.

Recently, infection of humans with avian influenza (e.g., H7N9 or H5N1) and a sign of a global outbreak thereof have been observed, and avian influenza has shown an infection fatality rate as high as from 30% to 60%. It has begun to be understood that a main cause of death is fulminant ARDS (hereinafter abbreviated as FARDS), that is, fulminant acute pneumonia, which occurs as a result of an excessive immune response on a host side, rather than a direct influence of growth of a virus. Therefore, it is an urgent task to establish a treatment method in preparation for a future pandemic.

ARDS and FARDS are distinguished on the basis of a ratio of an oxygen partial pressure in arterial blood to fraction of inspired oxygen (P/F ratio). A healthy individual has a P/F ratio of from about 400 to about 500. A case in which the P/F ratio is 300 or less is determined as acute lung injury (ALI), a case in which the P/F ratio is 200 or less is determined as ARDS, and a case in which the P/F ratio is 100 or less is determined as FARDS. ALI is an acute and progressive respiratory disease caused by, for example, sepsis, pneumonia, trauma, or aspiration, and exacerbation thereof leads to ARDS or FARDS.

A CD69 molecule (hereinafter sometimes referred to simply as CD69) is a type II membrane molecule belonging to the c-type lectin family, and is widely used as an early activation marker molecule to serve as an index of activation of lymphocytes. T cells and B cells both express CD69 within a few hours after stimulation. In addition, activated neutrophils, eosinophils, NK cells, and macrophages express CD69 on their cell surfaces. Meanwhile, in platelets, monocytes, and Langerhans cells, constitutive expression of CD69 is found. Functions of CD69 include a role as a co-receptor molecule, and possible involvement as an intercellular adhesion molecule in accumulation and infiltration of cells, but details thereof have not been understood very well.

CITATION LIST

Patent Literature

[PTL 1] JP 2007-022993 A
[PTL 2] WO 2013/161814 A1
[PTL 3] US 2012/0121503 A1
[PTL 4] U.S. Pat. No. 8,440,195 B2
[PTL 5] US 2013/0224111 A1
[PTL 6] JP 2012-102100 A
[PTL 7] JP 5938876 B2

Non Patent Literature

[NPL 1] Murata, K., et al.: CD69-null mice protected from arthritis induced with anti-type II collagen antibodies. Int. Immunol. 15: 987-992 (2003).
[NPL 2] Hasegawa, A., et al.: CD69 controls the pathogenesis of allergic airway inflammation. J. Immunol. 183: 8203-8215 (2009).
[NPL 3] Hasegawa, A., et al.: Crucial role for CD69 in the pathogenesis of dextran sulphate sodium-induced colitis. PLoS ONE 8 (6): e65494 (2013).
[NPL 4] Yamauchi, K., et al.: Attenuation of lung inflammation and fibrosis in CD69-deficient mice after intratracheal bleomycin. Respiratory Research 12: 131 (2011).
[NPL 5] Kohler, G. and Milstein, C.: Continuous cultures of fused cells secreting antibody of predefined specificity. Nature 256 (5517): 495-497 (1975).
[NPL 6] Eppstein, D. A., et al.: Biological activity of liposome-encapsulated murine interferon gamma is mediated by a cell membrane receptor. Proc. Natl. Acad. Sci. USA 82 (11): 3688-3692 (1985).

[NPL 7] Hwang, K. J., et al.: Hepatic uptake and degradation of unilamellar sphingomyelin/cholesterol liposomes: a kinetic study. Proc. Natl. Acad. Sci. USA 77 (7): 4030-4034 (1980).

[NPL 8] Martin, F. J., et al.: Irreversible coupling of immunoglobulin fragments to preformed vesicles. An improved method for liposome targeting. J. Biol. Chem. 257 (1): 286-288 (1982).

[NPL 9] Gabizon, A., et al.: Pharmacokinetics and Tissue Distribution of Doxorubicin Encapsulated in Stable Liposomes With Long Circulation Times. J. National Cancer Inst. 81 (19): 1484-1488 (1989).

[NPL 10] Hermann, T. and Patel, D. J.: Adaptive Recognition by Nucleic Acid Aptamers. Science 287 (5454): 820-825 (2000).

[NPL 11] Burgstaller, P. et al.: Aptamers and aptazymes: accelerating small molecule drug discovery. Curr. Opin. Drug Discov. Devel. 5 (5): 690-700 (2002).

[NPL 12] Hoppe-Seyler, F., et al.: Peptide Aptamers: Specific Inhibitors of Protein Function. Curr. Mol. Med. 4 (5): 529-538 (2004).

[NPL 13] Aagaard, L., et al.: A facile lentiviral vector system for expression of doxycycline-inducible shRNAs: knockdown of the pre-miRNA processing enzyme Drosha. Mol. Ther. 15 (5): 938-45 (2007).

[NPL 14] Aoyagi, T., et al.: Activation of pulmonary invariant NKT cells leads to exacerbation of acute lung injury caused by LPS through local production of IFN-gamma and TNF-alpha by Gr-1$^+$ monocytes. Int. Immunol. 23 (2): 97-108 (2010).

[NPL 15] Landgraf M. A. et al.: Leptin Downregulates LPS-Induced Lung Injury: Role of Corticosterone and Insulin. Cell. Physiol. Biochem. 33: 835-846 (2014).

[NPL 16] Huo M., et al.: Anti-inflammatory effects of linalool in RAW 264.7 macrophages and lipopolysaccharide-induced lung injury model. J. Surg. Res. 180 (1): e47-54 (2013).

[NPL 17] Weiser J. N., et al.: Macrophage Migration Inhibitory Factor Is Detrimental in Pneumococcal Pneumonia and a Target for Therapeutic Immunomodulation. J. Infect. Dis. 212: 1677-1682 (2015).

[NPL 18] Wilson, R., et al.: Protection against *Streptococcus pneumoniae* lung infection after nasopharyngeal colonization requires both humoral and cellular immune responses. Mucosal Immunol. 8 (3): 627-623 (2015).

[NPL 19] Kamata, T., et al.: src homology 2 domain-containing tyrosinephosphatase SHP-1 controls the development of allergic airway inflammation. J. Clin. Invest. 111 (1): 109-119 (2003).

[NPL 20] Vintersten, K., et al.: Mouse in red: red fluorescent protein expression in mouse ES cells, embryos, and adult animals. Genesis 40 (4): 241-256 (2004).

SUMMARY OF INVENTION

Technical Problem

The inventors of the present invention have previously generated and analyzed CD69 knockout mice to reveal, for example, that CD69 molecules on neutrophils are important for the development of arthritis (Non Patent Literature 1), and that allergic asthma and colitis do not occur in CD69 knockout mice (Non Patent Literatures 2 and 3). In addition, the inventors have disclosed therapeutic drugs for allergic asthma (Patent Literatures 1 and 2), therapeutic drugs for colitis (Patent Literatures 3 and 4), and therapeutic drugs for hepatitis (Patent Literatures 3 and 5 to 7) each targeting the CD69 molecule. In addition, there is a report that, in the CD69 knockout mice, lung inflammation and fibrosis induced by intratracheal administration of bleomycin were relieved as compared to those in wild-type mice (Non Patent Literature 4). However, a model of pneumonia induced by intratracheal administration of bleomycin is a model in which epithelial cells themselves have undergone fibrosis, and is a model of pneumonia different from fulminant acute pneumonia. Hitherto, the role of CD69 in the development or aggravation of fulminant acute pneumonia has not been known.

In view of the foregoing, an object of the present invention is to provide effective means for preventing and/or treating fulminant acute pneumonia.

Solution to Problem

In order to achieve the above-mentioned object, the inventors of the present invention have analyzed mechanisms by which FARDS is developed and becomes fulminant, and have made an extensive search for a therapeutic target molecule for the purpose of developing a novel treatment method. Then, the inventors have found that: symptoms of FARDS in a mouse FARDS model, such as a high mortality rate and remarkable infiltration of neutrophils into the lungs, are relieved by administering an antibody that specifically recognizes CD69 (hereinafter referred to as anti-CD69 antibody); and infiltration of CD69 knockout mouse-derived neutrophils into the lungs is reduced in the mouse FARDS model. In addition, the inventors have revealed that a CD69 molecule can serve as a target molecule for a novel treatment method for FARDS, and thus have completed the present invention.

That is, the present invention relates to a pharmaceutical composition for preventing and/or treating fulminant acute pneumonia, comprising a CD69 antagonist.

The present invention also relates to the pharmaceutical composition, wherein the CD69 antagonist is an anti-CD69 antibody.

The present invention also relates to a preventive agent and/or therapeutic agent for fulminant acute pneumonia, comprising a CD69 antagonist.

The present invention also relates to a preventive agent and/or therapeutic agent for fulminant acute pneumonia, comprising an antibody that specifically recognizes CD69.

The present invention also relates to a method of preventing and/or treating fulminant acute pneumonia, comprising administering a CD69 antagonist to a subject diagnosed to be in need of prevention and/or treatment of fulminant acute pneumonia, at an effective dose for the prevention and/or treatment of the pneumonia.

The present invention also relates to the method, wherein the CD69 antagonist is an anti-CD69 antibody.

Advantageous Effects of Invention

According to the present invention, the pharmaceutical composition for preventing and/or treating fulminant acute pneumonia containing the CD69 antagonist, such as the anti-CD69 antibody, and the preventive agent and/or therapeutic agent for fulminant acute pneumonia containing the CD69 antagonist can be provided.

According to the present invention, the method of preventing and/or treating fulminant acute pneumonia comprising administering the CD69 antagonist, such as the anti-CD69 antibody, can also be provided.

Fulminant acute pneumonia developed in a patient receiving artificial respiration in an intensive care unit or the like or developed owing to infection with highly pathogenic avian influenza is characterized by rapid development and subsequent rapid progression of disease state, and has a poor prognosis and an extremely high risk of death. The present invention can provide novel and revolutionary therapy in the treatment of fulminant acute pneumonia, for which no effective treatment method has heretofore been developed.

The pharmaceutical composition according to the present invention has shown effective therapeutic effects in both administration before the development of fulminant acute pneumonia and administration after the development, and hence can be used for both preventing and treating fulminant acute pneumonia, thereby highly contributing to a pharmaceutical field as a therapy in preparation for a future pandemic of avian influenza or the like.

BRIEF DESCRIPTION OF DRAWINGS

In FIG. 1C, No treatment represents the mouse administered only PBS and not developing FARDS, and treatment represents the mouse FARDS model (Example 1).

In FIG. 1D, No treatment represents the mice administered only PBS and not developing FARDS, and treatment represents the mouse FARDS model (Example 1).

In FIG. 3A, T lympho. means T lymphocytes, B lympho. means B lymphocytes, Mac. means macrophages, Neutro. means neutrophils, and total means all the cells (Example 3).

In FIG. 4, PBS/PBS represents a mouse not having FARDS induced, αGalCer/LPS represents a mouse having FARDS induced, and Anti-CD69 mAb represents a mouse having FARDS induced after anti-CD69 antibody administration (Example 4).

In FIG. 5A, Ab means antibody (Example 5).

In FIG. 5C, No treatment represents a mouse administered only PBS and not developing FARDS, and treatment represents the mouse FARDS model. In addition, Control mAb represents the control antibody (Example 5).

In FIG. 5D, (-) represents wild-type mice administered only PBS, αGC+LPS represents mice having FARDS developed by administering α-GalCel and LPS, and Control mAb represents mice administered the control antibody (Example 5).

In FIG. 6A, Ab means antibody (Example 6).

In FIG. 6C, No treatment represents a lung tissue image of a mouse administered only PBS and not developing FARDS, and Anti-CD69 mAb represents a lung tissue image when the anti-CD69 antibody was administered to the mouse FARDS model after the administration of LPS. In addition, Control mAb represents a lung tissue image when the control antibody was administered to the mouse FARDS model after the administration of LPS (Example 6).

In FIG. 7, WT neutrophil indicates an image for showing infiltration of wild-type mouse-derived neutrophils into the lungs. CD69KO neutrophil indicates an image for showing infiltration of CD69 knockout mouse neutrophils into the lungs. Merged indicates an image obtained by superimposing the above-mentioned two images. In addition, αGalCel/LPS represents the administration of αGalCel and LPS, and PBS/PBS represents the administration of PBS in place of αGalCel/LPS (Example 7).

DESCRIPTION OF EMBODIMENTS

Figure 1A:
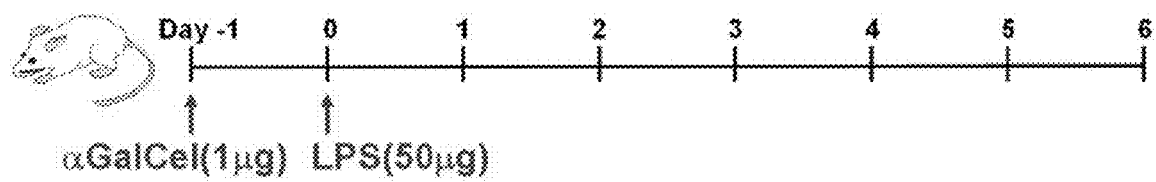
FIG. 1A is a diagram for describing a method of generating a mouse FARDS model. The mouse FARDS model was generated by transnasally administering α-galactosylceramide (hereinafter abbreviated as αGalCel) to wild-type mice (hereinafter, WT) (Day −1), and 24 hours after that, transnasally administering lipopolysaccharide (hereinafter abbreviated as LPS) thereto (Day 0) (Example 1).

The present invention relates to a pharmaceutical composition for preventing and/or treating fulminant acute pneumonia containing a CD69 antagonist. The present invention also relates to an agent for suppressing intra-alveolar neutrophil aggregation containing a CD69 antagonist. The present invention also relates to an agent for suppressing pulmonary neutrophil infiltration. The present invention also relates to a preventive agent and/or therapeutic agent for fulminant acute pneumonia containing a CD69 antagonist.

The present invention also relates to a method of preventing and/or treating fulminant acute pneumonia comprising administering a CD69 antagonist to each of a subject diagnosed to have a risk of developing fulminant acute pneumonia and a subject diagnosed with fulminant acute pneumonia, at an effective dose for preventing and/or treating fulminant acute pneumonia.

The present invention also relates to a method of preventing and/or treating fulminant acute pneumonia comprising administering a CD69 antagonist to a subject diagnosed to be in need of suppression of intra-alveolar neutrophil aggregation, at an effective dose for the suppression.

The present invention also relates to a method of preventing and/or treating fulminant acute pneumonia comprising administering a CD69 antagonist to a subject diagnosed to be in need of suppression of pulmonary neutrophil infiltration, at an effective dose for the suppression.

Herein, the term "fulminant acute pneumonia" is interchangeably used with the term "fulminant acute respiratory distress syndrome (FARDS)."

The "fulminant acute respiratory distress syndrome (FARDS)" refers to a respiratory distress syndrome showing more severe symptoms as compared to acute respiratory distress syndrome (ARDS). ARDS refers to a pathological condition characterized by acute respiratory failure based on a disorder in the intake of oxygen into the body through respiration. The respiration refers to an activity involving the intake of atmospheric oxygen into the body and the discharge of carbon dioxide produced in the body into inspired air. The intake of oxygen into the body is performed through: a step of delivering air from the mouth and nasal cavity through the respiratory tract to the alveoli (step 1); a step of performing gas exchange in the lungs, that is, a step in which oxygen is taken into alveolar epithelial cells from the air in the alveoli, and subsequently passes through tissue stroma and then vascular endothelial cells to bind to hemoglobin contained in red blood cells in blood (step 2); and a step of transporting the oxygen from the heart throughout the entire body through the utilization of blood circulation (step 3). A state in which a disorder has occurred in any one of those steps for some reason to prevent the oxygen from being sufficiently carried throughout the entire body is referred to as respiratory failure. ARDS refers to a pathological condition characterized by acute respiratory failure that has occurred within 48 hours based on a disorder mainly in the step of performing gas exchange in the lungs (the above-mentioned step 2) in the process of oxygen intake into the body.

According to a consensus conference between the American Thoracic Society and the European Society of Intensive Care Medicine (American-European Consensus Conference: AECC), ARDS is defined as "having a previously underlying disease, involving acute onset of hypoxemia, having bilateral pulmonary infiltrates found on a chest X-ray image, and allowing the exclusion of cardiogenic pulmonary edema." That is, ARDS does not refer to a specific disease, but refers to a syndrome showing symptoms characterized by acute development, evident hypoxemia, the presence of abnormal shadows across the entirety of a chest X-ray image, and noncardiogenic pulmonary edema. The pathological condition of ARDS includes: the accumulation of activated neutrophils into the lungs; the production of active oxygen and proteases by cells such as neutrophils; damage to capillaries in the alveolar walls and to pulmonary epithelial cells by the produced substances; the leakage of liquid components from the capillaries; resulting induction of edema; and findings of diffuse alveolar damage found in microscopy. A mortality rate after the development of ARDS is more than 43%. Examples of the previously underlying disease may include direct disorders, such as severe pneumonia and aspiration pneumonia, and indirect disorders, such as sepsis. It is recognized that about 80% of ARDS and ALI cases involve sepsis.

In the definition presented by the AECC in 1994 (AECC definition), a case in which the P/F ratio was 300 or less was determined as acute lung injury (ALI), and a case in which the P/F ratio was 200 or less was determined as ARDS. However, in a new definition presented in 2012 (Berlin definition), a case in which the P/F ratio is 300 or less is determined as mild ARDS, a case in which the P/F ratio is 200 or less is determined as ARDS, and a case in which the P/F ratio is 100 or less is determined as severe ARDS. The term "mild ARDS" and the term "ALI" are interchangeably used herein. In addition, the term "severe ARDS" and the term "FARDS" are interchangeably used herein. A healthy individual has a P/F ratio of from about 400 to about 500 (arterial oxygen partial pressure ($PaO_2$): 80 Torr (mmHg) to 100 Torr (mmHg)).

As compared to ARDS, FARDS involves more rapid occurrence of symptoms and more rapid progression of pneumonia, and has a poorer prognosis, that is, is more liable to become severe, and also has a higher risk of death. In recent years, it has been reported that infection with an influenza virus of avian influenza (e.g., H7N9 or H5N1) or the like causes FARDS, showing an infection fatality rate as high as from 30% to 60%. It has begun to be understood that the condition becoming fulminant and the high fatality rate in FARDS occur as a result of an excessive immune response on a host side to the virus rather than a direct influence of the growth of the virus. In an inflammation such as pneumonia, a histological disorder or a pathological state results from a complete or partial series of defense responses of a living body to various damaging factors acting on the living body, such as a change in the number of immune system cells, a change in migration speed of the cells, and a change in activity of the cells.

Examples of the immune system cells involved in the defense responses of the living body may include T cells, B cells, monocytes or macrophages, antigen-presenting cells (APC), dendritic cells, microglial cells, NK cells, NKT cells, neutrophils, eosinophils, mast cells, or any other cells specifically associated with immunity, such as cytokine-producing endothelial cells or cytokine-producing epithelial cells. FARDS caused by influenza virus infection is specifically considered to be as follows: excessive production of cytokines induced by the infection further induces infiltration of neutrophils and alveolar macrophages into the lungs, and as a result, alveolar epithelial cells subjected to the infiltration produce molecules that cause tissue damage.

The pharmaceutical composition, pharmaceutical agent, and method according to the present invention are applied to "fulminant acute pneumonia". One preferred embodiment of the present invention may be exemplified by fulminant acute pneumonia caused by infection with an influenza virus, more preferably FARDS caused by infection with an influenza virus. In such embodiment, examples of the influenza virus causing fulminant acute pneumonia may include so-called seasonal influenza viruses, such as Hong Kong influenza A, a Russian influenza A, and influenza B viruses, and a highly pathogenic avian influenza virus. Preferred examples of the avian influenza virus may include type H5N1 and type H1N1. It has been reported that a case of infection with the highly pathogenic avian influenza virus, or a case that has become severe after infection with a different type of virus may become fulminant in a short period of time through the induction of an acute respiratory disorder, sometimes progressing to multiple organ failure and possibly leading even to death.

The "preventing fulminant acute pneumonia" refers to taking some measure before the occurrence of fulminant acute pneumonia to preclude the occurrence of fulminant acute pneumonia or at least relieve symptoms after the occurrence.

The "treating fulminant acute pneumonia" refers to taking some measure to cause symptoms of fulminant acute pneumonia to disappear, relieve the symptoms, or stop the progression thereof.

The "CD69 antagonist" refers to a substance that suppresses the function of a signal transduction system in cells mediated by a CD69 molecule caused by binding of a ligand for CD69 to the CD69 molecule, to thereby inhibit the expression of the activity of the cells by the ligand. The "antagonist" is also called an antagonistic drug, an antagonistic agent, or a blocker.

The CD69 antagonist may be a substance that binds to CD69, but unlike a ligand serving as a biological substance binding to CD69, does not cause a biological reaction, and inhibits, through the binding, binding between the ligand and CD69, to suppress the function of the signal transduction system in cells mediated by CD69 with the ligand, to thereby inhibit the expression of the activity of the cells by the ligand. Examples of such substance may include an anti-CD69 antibody, a CD69 aptamer, and a low-molecular-weight pharmaceutical.

In addition, the CD69 antagonist may be a substance capable of causing a reduction in CD69 expression. Such substance may be any substance that inhibits the transcription and/or translation of a CD69 gene to suppress the expression of the gene. Examples of such substance may include a CD69 mRNA antagonist, a CD69 aptamer, small double-stranded RNA, and a low-molecular-weight pharmaceutical.

A preferred example of the CD69 antagonist may be an anti-CD69 antibody. Such anti-CD69 antibody is preferably an antibody that specifically recognizes CD69 and binds thereto. That the antibody specifically recognizes CD69 and binds thereto means that the antibody recognizes and binds to CD69, but does not recognize or weakly recognizes a protein other than CD69. The anti-CD69 antibody acting as the CD69 antagonist is an antibody that, unlike a ligand serving as a biological substance binding to CD69, does not cause a biological reaction, and has an action of inhibiting, through the binding, binding between the ligand and CD69, to suppress the function of the signal transduction system in cells mediated by CD69 with the ligand, to thereby inhibit the expression of the activity of the cells by the ligand.

The anti-CD69 antibody may be any of a monoclonal antibody and polyclonal antibodies, and may be a chimeric antibody and/or a humanized antibody. A non-human antibody may be humanized using a method known per se in a technical field relating to the production of an antibody. For example, the humanized antibody may be generated using a transgenic animal whose immune system has been partially or fully humanized. Any antibody or fragment thereof according to the present invention may be partially or fully humanized. The chimeric antibody may be generated using a method known per se in a technical field relating to the production of an antibody.

The anti-CD69 antibody may be generated using a CD69 polypeptide or a fragment peptide containing an epitope thereof as an antigen, by a method known per se in a technical field relating to the production of an antibody. In the generation of the anti-CD69 antibody, an amino acid sequence of the CD69 polypeptide may be exemplified by a sequence having an accession number of BAF84558, ABM87473, ABM84101, EAW96123, EAW96122, Q53ZX0, AAO63584, AAH07037, NP_001772, Q07108, CAA83017, CAA80298, or AAB46359, versions thereof, parts thereof, or combinations thereof.

The CD69 polypeptide or the fragment peptide containing the epitope thereof serving as the antigen to be used in the production of the anti-CD69 antibody is preferably one appropriate for the kind of the subject to which the anti-CD69 antibody is to be administered. When the subject to which the anti-CD69 antibody is to be administered is a human, the anti-CD69 antibody is preferably an antibody against a human CD69 polypeptide or a fragment polypeptide containing an antigen-binding fragment thereof. A preferred example of such antibody may be an anti-human CD69 antibody disclosed in Patent Literature 2.

The production of the antibody may be, specifically, in the case of the production of polyclonal antibodies, carried out by causing an animal to produce antibodies by multiple subcutaneous (s.c.) or intraperitoneal (i.p.) injection of an antigen in combination with an adjuvant, such as Freund's adjuvant (complete or incomplete). In order to enhance immunogenicity, it is useful to first complex a polypeptide or fragment containing a target amino acid sequence with a protein having immunogenicity in the species to be immunized, such as keyhole limpet hemocyanin, serum albumin, bovine thyroglobulin, or a soybean trypsin inhibitor, through the use of a bifunctional pharmaceutical agent or a derivatizing agent, such as maleimidobenzoylsulfosuccinimide ester (complexing via a cysteine residue), N-hydroxysuccinimide (via a lysine residue), glutaraldehyde, succinic anhydride, or $SOCl_2$. Alternatively, an immunogenic complex may be generated as a fusion protein by a recombination technology.

The production of the monoclonal antibody may be carried out using a method known per se in a technical field relating to the production of an antibody, such as a hybridoma method described in a previous report (Non Patent Literature 5). In the hybridoma method, a mouse, a hamster, or any other appropriate host animal is typically immunized using an immunizing agent to produce an antibody that specifically binds to the immunizing agent or to induce lymphocytes capable of producing the antibody. Alternatively, lymphocytes may be immunized in vitro. The monoclonal antibody may be prepared by collecting spleen cells from an immunized animal, and immortalizing the cells by a conventional technique, such as fusion with myeloma cells. Prepared clones are then screened for one expressing a desired antibody. The monoclonal antibody is preferably one that does not cross-react with a protein other than CD69. After the identification of desired hybridoma cells, the clones may be subcloned by a limiting dilution procedure and grown by a standard method. The monoclonal antibody secreted by the subclones may be isolated or purified from a culture medium or ascites by a conventional immunoglobulin purification procedure, such as protein A-Sepharose, hydroxyapatite chromatography, gel electrophoresis, dialysis, or affinity chromatography.

In addition, in the present invention, a fragment of the anti-CD69 antibody (hereinafter referred to as antibody fragment), the antibody fragment containing an antigen-binding fragment of the anti-CD69 antibody, may be used in the same manner as the anti-CD69 antibody. The structure of the antibody fragment is not particularly limited as long as the antibody fragment has an action similar to the action of the anti-CD69 antibody. The antibody fragment contains part of an intact antibody, such as an antigen-binding region or variable region of the intact antibody. Examples of the antibody fragment include: a Fab fragment, a Fab1 fragment, a F(ab')2 fragment, and an Fv fragment; a diabody; a linear antibody; a single-chain antibody molecule; and a multispecific antibody formed from antibody fragments.

The antibody fragment may be generated by a method known per se in a technical field relating to the production of an antibody. For example, the Fab fragment is obtained by papain treatment of the antibody, and the F(ab')2 fragment is obtained by pepsin treatment of the antibody. In addition, a single-chain Fv or sFv antibody fragment contains the VH domain and VL domain of the antibody, and in this case, these domains are present in a single polypeptide chain. The Fv polypeptide may further contain, between the VH domain and the VL domain, a polypeptide linker that enables sFv to form a desired structure for antigen binding. The diabody is a small antibody fragment having two antigen-binding sites, and this fragment contains a heavy chain variable domain (VH) linked to a light chain variable domain (VL) in the same polypeptide chain (VH-VL). In order to enable pairing between two domains on the same chain, a short linker may be used to pair a domain with a complementary domain of another chain, to thereby form two antigen-binding sites.

The antibody may be formulated as immunoliposomes. Liposomes each containing the antibody may be generated by a method known per se (Non Patent Literatures 6 and 7). A particularly useful liposome may be produced by a reverse-phase evaporation method using a lipid composition containing phosphatidylcholine, cholesterol, and polyethylene glycol-derivatized phosphatidylethanolamine (PEG-PE). The Fab fragment of the antibody according to the present invention may be conjugated with the liposome through a disulfide exchange reaction (Non Patent Literature 8). Any therapeutic drug may be further incorporated into the liposome (Non Patent Literature 9).

An example of the CD69 antagonist may be an aptamer that specifically recognizes CD69 and binds thereto, to thereby inhibit binding between CD69 and its ligand. The aptamer may be any of a nucleic acid aptamer and a peptide aptamer, and specifically, may contain one or a plurality of RNAs, DNAs, and amino acids. Such aptamer may be acquired using a known method (Non Patent Literatures 10 to 12). For example, a library of oligonucleotides having variable regions with lengths in the range of from 18 nucleotides to 50 nucleotides is used as a template for a run-off transcription reaction for producing a random pool of RNA aptamers. The aptamer pool is then exposed to an unconjugated matrix in order to remove species having nonspecific interaction. Then, the remaining pool is incubated together with an immobilized target. Most of the aptamer species in the pool have low affinity for the target, and hence washing can leave a pool bound to a small amount of a more specific matrix. The pool is then eluted, precipitated, reverse-transcribed, and used as a template for run-off transcription. Such selection is carried out five times, and then a given amount is taken, and cloned and sequenced. The selection may be continued until similar sequences are collected with good reproducibility. Alternatively, aptamer production may be performed using a bead-based selection system. In this process, there is produced a library of beads in which respective beads are coated with a population of aptamers having identical sequences constituted of natural and modified nucleotides. The bead library, which may contain more than $1\times10^8$ unique sequences, is incubated together with CD69 or part thereof, such as a peptide corresponding to an extracellular domain, conjugated with a tag, such as a fluorescent dye. After washing, a bead showing the highest binding affinity is isolated, and its aptamer sequence is determined for subsequent synthesis. Thus, an aptamer having a desired function is obtained.

Another example of the CD69 antagonist may be a CD69 mRNA antagonist. An example of the mRNA antagonist may be at least one small interfering RNA (siRNA) or at least one ribozyme. According to the present invention, the CD69 antagonist may be a nucleic acid for therapeutic use, such as siRNA, and target a CD69 nucleotide sequence, a complement thereof, or any combination thereof. Any suitable CD69 sequence may be utilized. The CD69 target sequence of synthetic siRNA is designed for a human CD69 nucleotide sequence having an accession number of NM_001781, NR_026672, NR_026671, AK303383, AK303174, AK291869, DQ896474, DQ893175, CH471094, AY238518, BC007037, AC007068, Z38109, Z30426, Z22576, or L07555, or any part or combination thereof, or can recognize all or part of subsets of CD69 transcript variants.

The CD69 antagonist may be a nucleic acid that specifically binds to a target nucleic acid encoding CD69 or a complement thereof and has a length of at least 10 nucleotides complementary thereto. In this case, the administration of the CD69 antagonist includes introducing the nucleic acid into cells of the subject. RNA interference (RNAi) may be utilized, and the CD69 antagonist may be siRNA. The administration of the CD69 antagonist includes introduction into cells of the subject, and in this case, the cells may transiently express CD69 as an siRNA nucleic acid in an effective amount under conditions sufficient for interfering the expression of CD69. The siRNA nucleic acid may contain an overhang. That is, not all the nucleotides are necessarily required to bind to the target sequence. The siRNA nucleic acid may contain RNA. In addition, the siRNA nucleic acid may contain DNA, that is, deoxyribonucleic acid nucleotides. Any kind of suitable small interfering RNA may be utilized. Endogenous microRNA (miRNA) may be utilized. Examples of the other RNA interference agent that may be used in accordance with the present invention include short hairpin RNA (snRNA), trans-acting siRNA (tasiRNA), repeat-associated siRNA (ra-siRNA), small-scan RNA (scnRNA), and Piwi-interacting (pi) RNA (piRNA). The RNA interference nucleic acid to be utilized may have a length of at least 10 nucleotides, at least 15 nucleotides, 16 nucleotides, 17 nucleotides, 18 nucleotides, 19 nucleotides, 20 nucleotides, 21 nucleotides, 22 nucleotides, 23 nucleotides, 24 nucleotides, 25 nucleotides, 26 nucleotides, 27 nucleotides, 28 nucleotides, 29 nucleotides, 30 nucleotides, 31 nucleotides, 32 nucleotides, 33 nucleotides, 34 nucleotides, or at least 35 and/or 40 nucleotides to 50 nucleotides. An RNAi agent may include one or a plurality of deoxyribonucleotides. An RNAi agent, such as siRNA or shRNA, may be included as a cassette of a larger nucleic acid construct, such as an appropriate vector system. Examples of such vector system include a lentiviral vector system and an adenoviral vector system. A suitable example of the system is described in a report by Aagaard et al. (Non Patent Literature 13). When the RNAi agent is present as a part of a larger nucleic acid construct, the nucleic acid to be obtained may have a length longer than that of the included RNAi nucleic acid, for example, a length of more than 50 nucleotides. The RNAi agent to be utilized may or may not cleave target mRNA.

In addition to RNA interference, or as an alternative to RNA interference, another nucleic acid antagonist may be utilized. The CD69 antagonist may be a ribozyme that specifically cleaves an RNA molecule transcribed from a gene encoding CD69, and in this case, the ribozyme contains a target substrate-binding site and a catalytic sequence in the substrate-binding site (the substrate-binding site is complementary to part of the RNA molecule transcribed from the CD69 gene). The CD69 antagonist may be an antisense nucleic acid containing a nucleotide sequence complementary to at least 8 nucleotides of a nucleic acid encoding CD69 or a complement thereof. The antisense nucleic acid may be complementary to a CD69 sequence of a sufficient length and sequence content so that the antisense nucleic acid may not cross-react with a non-CD69 nucleotide sequence. Even when the cross-reaction occurs, no substantial detrimental side effect is caused in some cases.

The CD69 antagonist may be a low-molecular-weight pharmaceutical. For example, a CD69-disabling small peptide mimetic may be utilized. Such mimetic may be configured to have secondary structural features similar to those of the target protein CD69.

The CD69 antagonists may be used alone or in combination of any two or more kinds thereof. In addition, the CD69 antagonist may be utilized in combination with another pharmaceutical agent for preventing and/or treating fulminant acute pneumonia. Two or more therapeutic drugs including one or a plurality of the CD69 antagonists may be administered simultaneously, sequentially, or in combination. Therefore, when two or more therapeutic drugs are administered, the two or more therapeutic drugs do not need to be administered simultaneously or by the same method or at the same dose. When simultaneously administered, the two or more therapeutic drugs may be administered in the same composition or in different compositions. The two or more therapeutic drugs may be administered using the same administration route or different administration routes. When administered at different times, the therapeutic drugs may be administered before and after each other. The administration order of the two or more therapeutic drugs may be alternate. One or a plurality of the therapeutic drugs may each be changed in dose with time. One or a plurality of the therapeutic drugs may be changed in kind with time. When administered at separate times, an interval between two or more times of administration may be any period. When a plurality of times of administration are performed, the length of the period may be changed. The interval of the administration of the two or more therapeutic drugs may be 0 seconds, 1 second, 5 seconds, 10 seconds, 30 seconds, 1 minute, 5 minutes, 10 minutes, 15 minutes, 20 minutes, 30 minutes, 45 minutes, 1 hour, 1.5 hours, 2 hours, 2.5 hours, 3 hours, 4 hours, 5 hours, 7.5 hours, 10 hours, 12 hours, 15 hours, 18 hours, 21 hours, 24 hours, 1.5 days, 2 days, 3 days, 4 days, 5 days, 6 days, 7 days, 10 days, 13 days, 15 days, 20 days, or longer.

In carrying out the present invention, the use of a pharmaceutically acceptable carrier for formulating the CD69 antagonist into an administration amount suitable for each of systemic administration and local administration falls within the scope of the present invention. In order to be suitable for appropriate selection of the carrier and actual production, the composition related to the present invention, particularly a composition to be formulated as a solution may be administered parenterally, for example, by intravenous injection. A compound can be easily formulated into an administration amount suitable for oral administration by using a pharmaceutically acceptable carrier known in the art.

Examples of the pharmaceutical carrier may include a filler, an extender, a binder, a moisture imparting agent, a disintegrant, a lubricant, a diluent, and an excipient to be generally used according to the use form of the formulation. Those carriers are appropriately selected and used depending on the dosage form of the formulation to be obtained. The pharmaceutical carrier may be more specifically exemplified by water, a pharmaceutically acceptable organic solvent, collagen, polyvinyl alcohol, polyvinylpyrrolidone, a carboxyvinyl polymer, sodium alginate, water-soluble dextran, sodium carboxymethyl starch, pectin, xanthan gum, gum arabic, casein, gelatin, agar, glycerin, propylene glycol, polyethylene glycol, vaseline, paraffin, stearyl alcohol, stearic acid, human serum albumin, mannitol, sorbitol, and lactose. Those carriers may be appropriately used alone or in combination thereof depending on the dosage form of a pharmaceutical agent of interest. In addition, for example, a stabilizing agent, a microbicide, a buffering agent, a tonicity agent, a chelating agent, a surfactant, and a pH adjustor may be appropriately used. The stabilizing agent may be exemplified by human serum albumin and a typical L-amino acid, a sugar, and a cellulose derivative. The L-amino acid is not particularly limited, and for example, any of glycine, cysteine, and glutamic acid may be used. In addition, the sugar is not particularly limited, and for example, any of the following sugars may be used: monosaccharides, such as glucose, mannose, galactose, and fructose; sugar alcohols, such as mannitol, inositol, and xylitol; disaccharides, such as sucrose, maltose, and lactose; polysaccharides, such as dextran, hydroxypropyl starch, chondroitin sulfate, and hyaluronic acid; and derivatives thereof. In addition, the cellulose derivative is not particularly limited, and for example, any of the following derivatives may be used: methyl cellulose, ethyl cellulose, hydroxyethyl cellulose, hydroxypropyl cellulose, hydroxypropylmethyl cellulose, and sodium carboxymethyl cellulose. In addition, the surfactant is not particularly limited, and for example, any of an ionic surfactant and a nonionic surfactant may be used. The surfactant encompasses, for example, polyoxyethylene glycol sorbitan alkyl ester-based, polyoxyethylene alkyl ether-based, sorbitan monoacyl ester-based, and fatty acid glyceride-based surfactants. The buffering agent may be exemplified by boric acid, phosphoric acid, acetic acid, citric acid, ε-aminocaproic acid, glutamic acid, and/or salts corresponding thereto (e.g., alkali metal salts and alkaline earth metal salts thereof, such as a sodium salt, potassium salt, calcium salt, and magnesium salt thereof). The tonicity agent may be exemplified by sodium chloride, potassium chloride, a sugar, and glycerin. The chelating agent may be exemplified by sodium edetate and citric acid.

The dose range of the pharmaceutical composition according to the present invention is not particularly limited, and is appropriately selected in accordance with, for example, the dosage form, the administration route, the kind of disease, the properties of the subject (e.g., body weight, age, condition, and presence or absence of the use of any other pharmaceutical), and a judgment by a doctor in charge. An appropriate dose may be determined using a general conventional experiment for optimization well known in the art, but in general, for example, a dose per kg of the body weight of the subject falls within the range of from about 0.01 µg to about 1,000 mg, from about 0.05 µg to about 500 mg, from about 0.07 µg to about 300 mg, or from about 0.1 µg to about 100 mg. The administration amount may be administered once or in divided doses (2, 3, 4, 5, 6, 7, 8, 9, or 10 doses) daily.

With regard to the dose of the CD69 antagonist contained in the pharmaceutical composition according to the present invention, a preferred dose varies depending on the kind of the CD69 antagonist, but can be easily determined by carrying out a simple repeated experiment using a fulminant acute pneumonia model animal or the like. For example, on the basis of the fact that an effect in a mouse fulminant acute pneumonia model has been found in administration at 200 µg/day (see Examples 4 to 6 to be described later), in consideration of, for example, the neutralizing antibody titer of the antibody, the preferred daily dose of the anti-CD69 antibody is from 0.5 mg/kg to 100 mg/kg, preferably from 0.5 mg/kg to 50 mg/kg, more preferably from 0.5 mg/kg to 20 mg/kg, still more preferably from 0.5 mg/kg to 10 mg/kg, yet still more preferably from 0.5 mg/kg to 10 mg/kg, even more preferably from 0.5 mg/kg to 2.5 mg/kg.

The amount of the active ingredient to be contained in the pharmaceutical composition according to the present invention is appropriately selected from a wide range. The amount generally falls within the range of from about 0.00001 wt % to about 70 wt %, from about 0.00005 wt % to about 50 wt %, from about 0.00007 wt % to about 30 wt %, or from about 0.0001 wt % to about 5 wt %.

Any of systemic administration and local administration may be selected as an administration route. In this case, an appropriate administration route is selected depending on a disease, a symptom, or the like. The pharmaceutical agent according to the present invention may be administered through any of an oral route and a parenteral route. Examples of the parenteral route may include subcutaneous administration, intradermal administration, and intramuscular administration as well as general intravenous administration and intraarterial administration.

A dosage form is not particularly limited, and various dosage forms may be adopted. For example, the composition may be used as a solution formulation, and the solution formulation may be lyophilized so as to be storable and then dissolved in, for example, a buffer solution containing water, physiological saline, or the like so as to be prepared at an appropriate concentration before use. In addition, a sustained dosage form and an extended release dosage form may each also be adopted.

Specifically, for the oral administration, there may be given a tablet, a capsule, a powder, a granule, a pill, a liquid, an emulsion, a suspension, a solution, a spirit, a syrup, an extract, or an elixir. As a parenteral agent, there may be given, but not limited to, for example: an injection, such as a subcutaneous injection, an intravenous injection, an intramuscular injection, or an intraperitoneal injection; a transdermal administration and a patch; an ointment and a lotion; a sublingual formulation or an oral patch for intraoral administration; an aerosol for transnasal administration; and a suppository. Those formulations may each be produced by a known method to be generally used in a formulation process.

In the case of preparing a solid formulation for oral administration, a tablet, a coated tablet, a granule, a powder, a capsule, or the like may be produced by using a conventional method after adding an excipient, and as required, a binder, a disintegrant, a lubricant, a colorant, a taste-masking agent, an odor-masking agent, or the like to the above-mentioned active ingredient. An additive to be generally used in the art may be adopted as such additive. Examples of the excipient may include lactose, saccharose, sodium chloride, glucose, starch, calcium carbonate, kaolin, microcrystalline cellulose, and silicic acid. Examples of the binder may include water, ethanol, propanol, simple syrup, glucose solution, starch solution, gelatin solution, carboxymethyl cellulose, hydroxypropyl cellulose, hydroxypropyl starch, methyl cellulose, ethyl cellulose, shellac, calcium phosphate, and polyvinylpyrrolidone. Examples of the disintegrant may include dry starch, sodium alginate, powdered agar, sodium hydrogen carbonate, calcium carbonate, sodium lauryl sulfate, stearic acid monoglyceride, and lactose. Examples of the lubricant may include purified talc, a stearate, borax, and polyethylene glycol. Examples of the taste-masking agent may include saccharose, orange peel, citric acid, and tartaric acid.

In the case of preparing a liquid formulation for oral administration, an oral liquid, a syrup, an elixir, or the like may be produced by using a conventional method after adding a taste-masking agent, a buffering agent, a stabilizing agent, an odor-masking agent, or the like to the above-mentioned compound. In this case, the taste-masking agent may be any of the agents listed above, an example of the buffering agent may be sodium citrate, and examples of the stabilizing agent may include tragacanth, gum arabic, and gelatin.

In the case of preparing an injection, subcutaneous, intramuscular, and intravenous injections may each be produced by using a conventional method after adding a pH adjustor, a buffering agent, a stabilizing agent, a tonicity agent, a local anesthetic, or the like to the above-mentioned compound. Examples of the pH adjustor and the buffering agent in this case may include sodium citrate, sodium acetate, and sodium phosphate. Examples of the stabilizing agent may include sodium pyrosulfite, ethylenediaminetetraacetic acid (EDTA), thioglycolic acid, and thiolactic acid. Examples of the local anesthetic may include procaine hydrochloride and lidocaine hydrochloride. Examples of the tonicity agent may include sodium chloride and glucose.

The CD69 antagonist may be provided as an agent for suppressing intra-alveolar neutrophil aggregation or an agent for suppressing pulmonary neutrophil infiltration.

The "suppression of intra-alveolar neutrophil aggregation" refers to reducing intra-alveolar aggregation or accumulation of neutrophils, for example, intra-alveolar aggregation or accumulation of neutrophils observed in a disease such as FARDS.

The "suppression of pulmonary neutrophil infiltration" refers to inhibiting invasion of neutrophils into the lungs, for example, invasion of neutrophils into lungs observed in a disease such as FARDS.

The CD69 antagonist may also be provided as a preventive agent and/or therapeutic agent for fulminant acute pneumonia containing a CD69 antagonist.

The present invention is hereinafter described more specifically by way of Examples. However, the technical scope of the present invention is not limited thereto.

EXAMPLE 1

Fulminant acute pneumonia was induced in wild-type mice (mouse FARDS model), and the mortality rate, lung findings, and P/F ratio were investigated. For the mice, wild-type C57BL/6 mice were used. All animal care was carried out in accordance with the guideline of Yamaguchi University.

The mouse FARDS model was generated by: transnasally administering a solution prepared by dissolving α-galactosylceramide (αGalCel; manufactured by KIRIN), an activator for NKT cells, in pyrogen-free phosphate buffered saline (PBS) to wild-type mice at a dose of 1 μg/50 μl PBS/mouse to sensitize the mice (Day −1); and after 24 hours, transnasally administering a solution prepared by dissolving lipopolysaccharide (LPS) in pyrogen-free PBS at a dose of 50 μg/50 μl PBS/mouse (Day 0) to induce fulminant acute pneumonia (FIG. 1A). It has been previously reported that, fulminant acute pneumonia is induced when LPS is administered to wild-type mice after the administration of αGalCel (Non Patent Literature 14).

After the LPS administration, the mice were each confirmed to be dead or alive every 12 hours to calculate the survival rate. After 48 hours from the LPS administration, arterial blood was collected from each of the mice, and measured for an arterial oxygen partial pressure using an automatic analyzer (ABS555, Radiometer Copenhagen, Denmark) to calculate the P/F ratio. For histological analysis, a lung obtained from each of the mice after 72 hours from the LPS administration was fixed in 4% paraformaldehyde and embedded in paraffin to prepare a section, which was subjected to hematoxylin-eosin (H&E) staining for histological examination. The sample was examined under an optical microscope.

1. Mortality Rate in Mouse FARDS Model

Figure 1B:
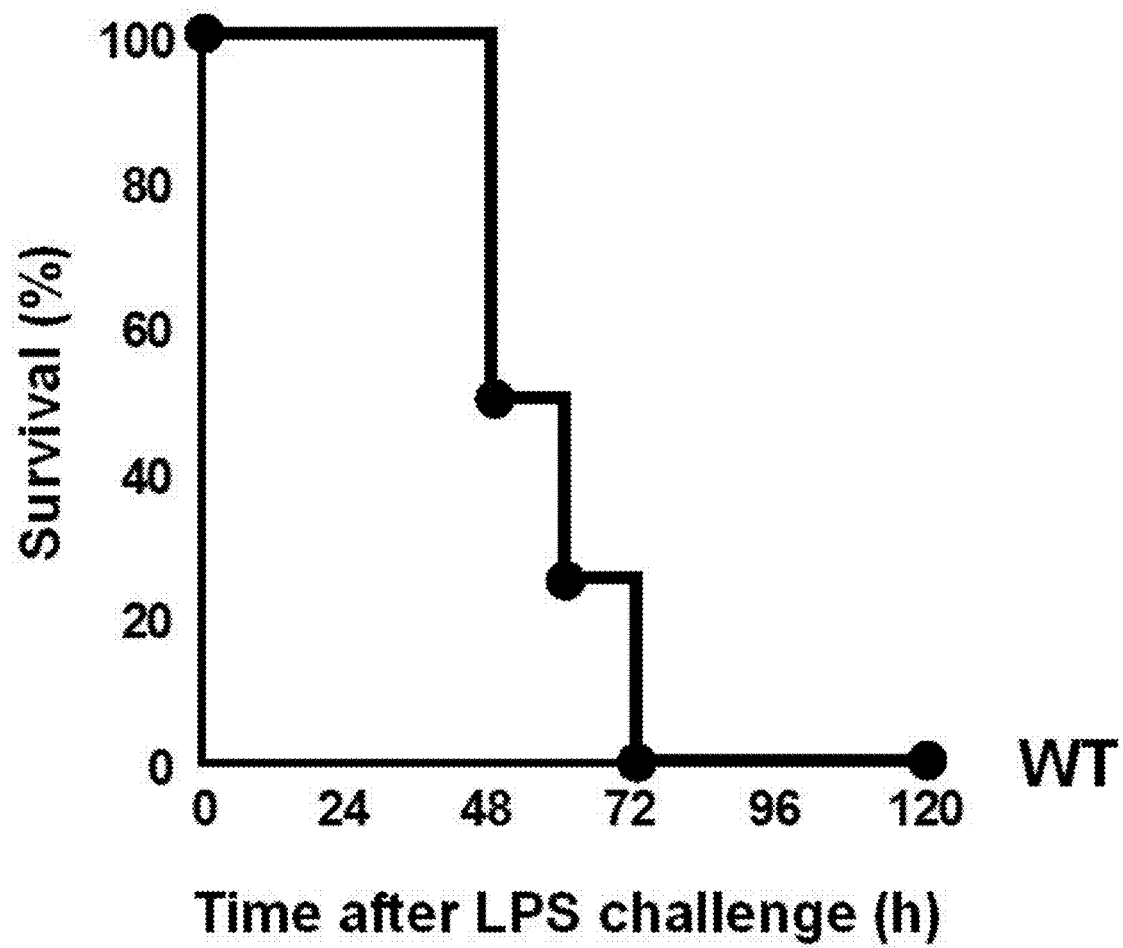
FIG. 1B is a graph for showing the results of a temporal investigation of the survival rate of the mouse FARDS model (see FIG. 1A) after LPS administration. The vertical axis of the graph represents survival rate (Survival (%)), and the horizontal axis represents time after LPS administration (Time after LPS challenge (h)) (Example 1).

An investigation was performed using eight FARDS model mice, and as a result, 80% or more thereof died in 2 to 3 days after the LPS administration (FIG. 1B).

2. Lung Findings in Mouse FARDS Model

Figure 1C:
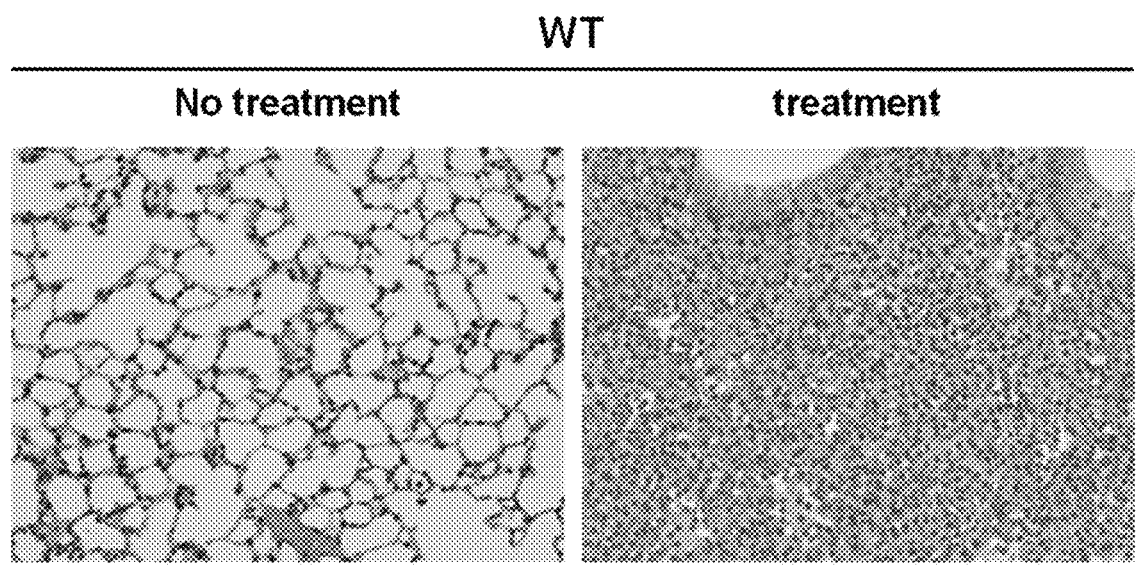
FIG. 1C are photographs for describing that, in the mouse FARDS model, remarkable neutrophil infiltration into the lungs was found as compared to a mouse administered only phosphate buffered saline (hereinafter abbreviated as PBS) and not developing FARDS.

In the mouse FARDS model, 72 hours after the LPS administration, extremely intense neutrophil infiltration was observed in the lung tissue as in a histopathological image of human ARDS/FARDS (FIG. 1C).

3. P/F Ratio in Mouse FARDS Model

Figure 1D:
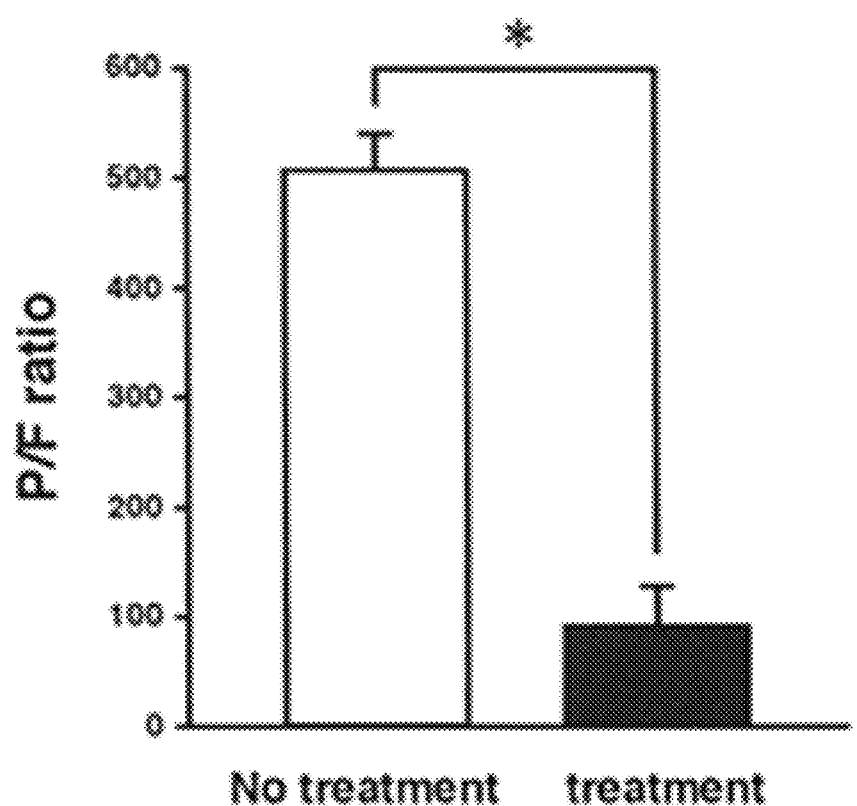
FIG. 1D is a graph for describing that the mouse FARDS model had a significantly low P/F ratio as compared to mice administered only PBS and not developing FARDS.

P/F ratio was 91.8±34.6 in the mouse FARDS model. Meanwhile, in the non-treated wild-type mice (hereinafter referred to as wild-type mice in a steady state), P/F ratio was 507.1±31.9. These results revealed that the P/F ratio of the wild-type mice in a steady state was comparable to or slightly higher than that of humans, whereas the P/F ratio of the mouse FARDS model was equivalent to that of human FARDS (FIG. 1D).

EXAMPLE 2

Infiltration of neutrophils and CD4 T cells into the lungs in a mouse FARDS model was quantitatively measured by visualizing immune cells using an imaging technology.

Figure 2A:
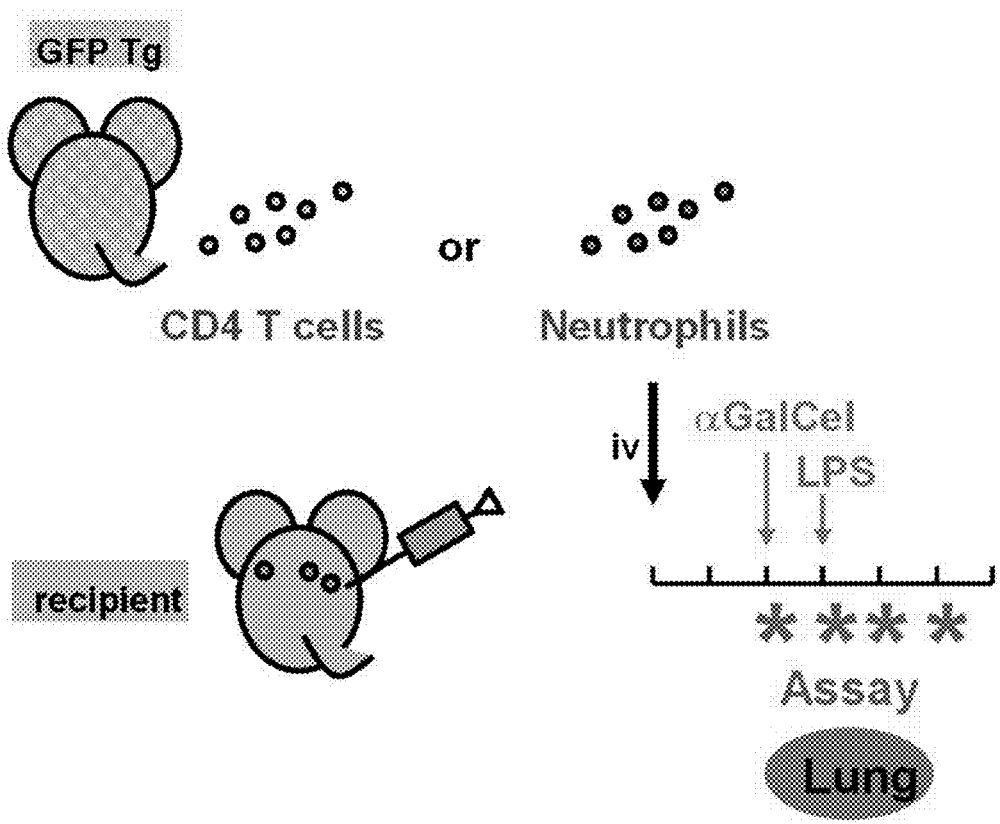
FIG. 2A is a diagram for describing an imaging technology used to investigate neutrophil infiltration into the lungs in the mouse FARDS model. A transgenic mouse having incorporated therein a green fluorescent protein gene (hereinafter referred to as GFP Tg) was used as a donor, and neutrophils and CD4 T cells were collected therefrom. Then, a wild-type mouse was used as a recipient, and the neutrophils and the CD4 T cells were transfused thereto intravenously (iv). αGalCel was administered 48 hours after that, and further, LPS was administered 24 hours after that. After 6 hours, 12 hours, 24 hours, and 48 hours from the LPS administration, neutrophil infiltration into the lungs (Lung) was observed (Example 2).

The mouse FARDS model was generated as described below (FIG. 2A). Transgenic mice having a green fluorescent protein transgene (hereinafter referred to as GFP Tg) were used as donors, and neutrophils and CD4 T cells were purified from the femur bone marrow thereof using an AutoMACS sorter (Miltenyi Biotec) to a purity of 98% each. GFP Tg (C57BL/6-Tg (CAG-EGFP)C14-Y01-FM131Osb mice) was purchased from the RIKEN BioResource Center. The isolated 2,000,000 neutrophils or CD4 T cells were intravenously (iv) administered into wild-type C57BL/6 mice (Day −3). Then, syngeneic wild-type mice, i.e., C57BL/6 mice were used as a recipient, and the neutrophils or CD4 T cells were intravenously transfused thereto. After 48 hours from the cell transfusion (Day −1), αGalCel was transnasally administered to the wild-type mice at a dose of 1 μg/50 μl PBS/mouse, and after 24 hours (Day 0), LPS was transnasally administered thereto at a dose of 50 μg/50 μl PBS/mouse to induce fulminant acute pneumonia.

After 6 hours, 12 hours, 24 hours, and 48 hours from the LPS administration, the lungs of the mice were removed, and GFP-positive neutrophils were observed using a fluorescence microscope (M250FA, manufactured by Nikon Corporation).

1. Neutrophil Accumulation into Lungs of Mouse FARDS Model

Figure 2B:
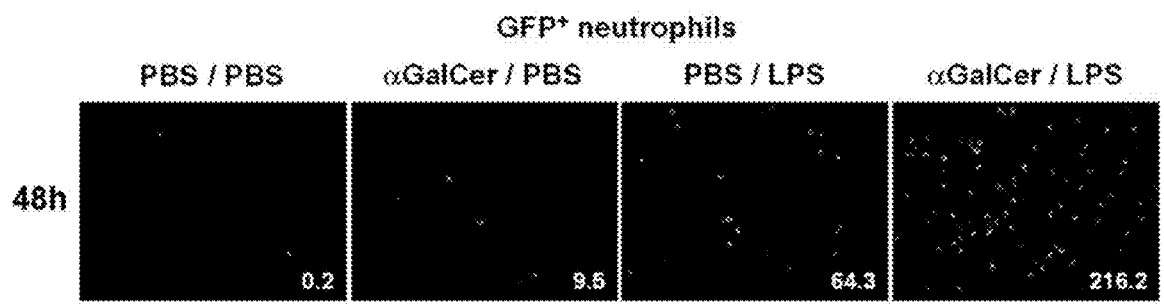
FIG. 2B are photographs for showing the results of measurement of neutrophil infiltration into the lungs 48 hours after LPS administration in the mouse FARDS model. In mice administered αGalCel and LPS, remarkable infiltration of GFP-positive neutrophils (GFP+ neutrophils) into the lungs was found as compared to mice administered only PBS, mice administered αGalCel and PBS, and mice administered PBS and LPS (Example 2).

In the mice administered αGalCel and LPS, extremely intense infiltration of GFP-positive neutrophils in the lung tissue was observed at 48 hours after the LPS administration (FIG. 2B). In the mice administered only LPS, infiltration of neutrophils into the lungs was also found, but the number of infiltrating neutrophils was smaller than that in the mice administered αGalCel and LPS. These results revealed that neutrophil infiltration into the lungs induced by LPS was dramatically increased by pre-administering αGalCel. In addition, the infiltrating neutrophils were observed to be aggregated to a degree that the neutrophils contacted with each other. The formation of an aggregate by the infiltrating neutrophils in the lungs is one of the features of fulminant acute pneumonia. In the reported cases of pneumonia other than fulminant acute pneumonia, for example, pneumonia in an animal experimentally developed by administering LPS or bacterial cells, the neutrophils are included only to such a degree as to be scattered in the alveoli (Non Patent Literatures 15 to 18). In the mice administered αGalCel and LPS, in addition to the transfused GFP-positive neutrophils, non-GFP-labeled neutrophils originally existed in the recipient infiltrate the lungs in large numbers, and form aggregates of neutrophils. These results suggest that the administration of αGalCel and LPS dramatically increases neutrophil infiltration into the lungs to form aggregates, to thereby make pneumonia fulminant.

2. Temporal Change in Neutrophil Accumulation in Lung after LPS Administration

Figure 2C:
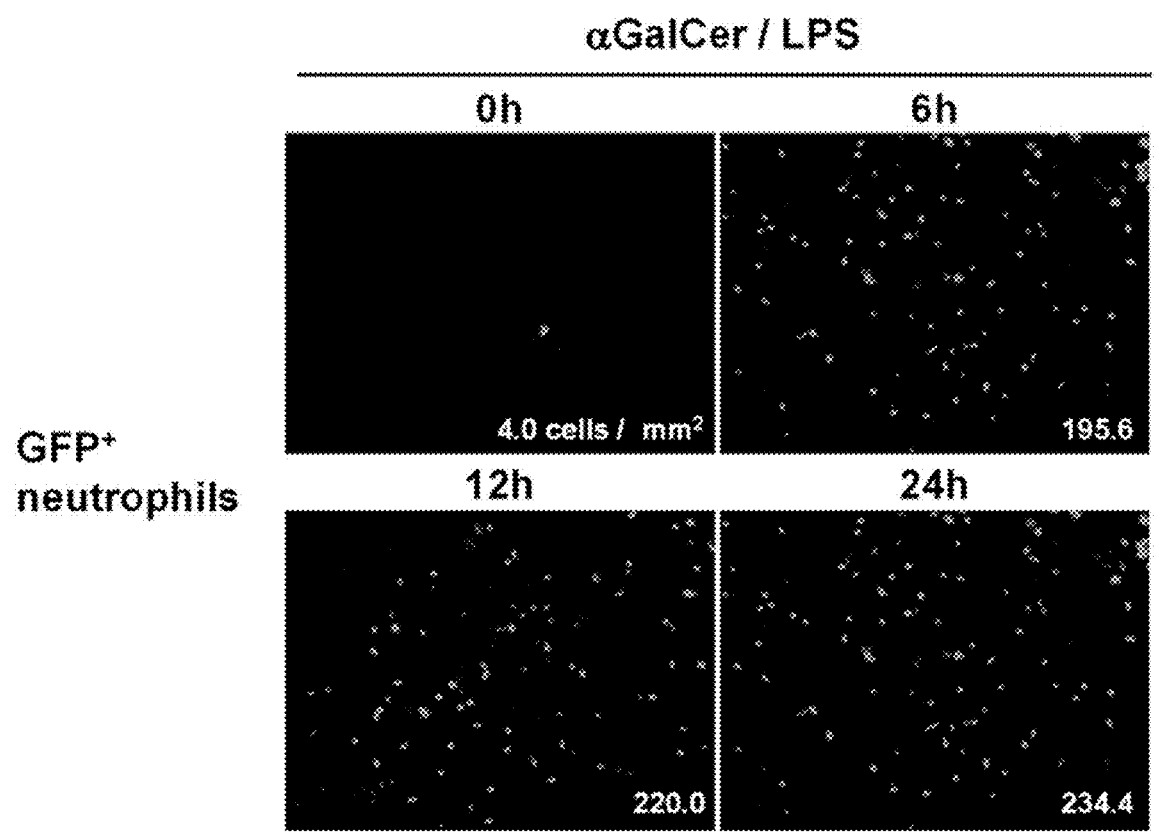
FIG. 2C are photographs for showing the results of temporal measurement of neutrophil infiltration into the lungs in the mouse FARDS model. Remarkable infiltration of GFP-positive neutrophils (GFP+ neutrophils) into the lungs was found in about 6 hours after LPS administration (Example 2).

In the mice administered αGalCel and LPS, remarkable infiltration of GFP-positive neutrophils into the lungs was found in about 6 hours after the administration of LPS (FIG. 2C).

3. Temporal Change in CD4 T Cell Accumulation in Lungs after LPS Administration

Figure 2D:
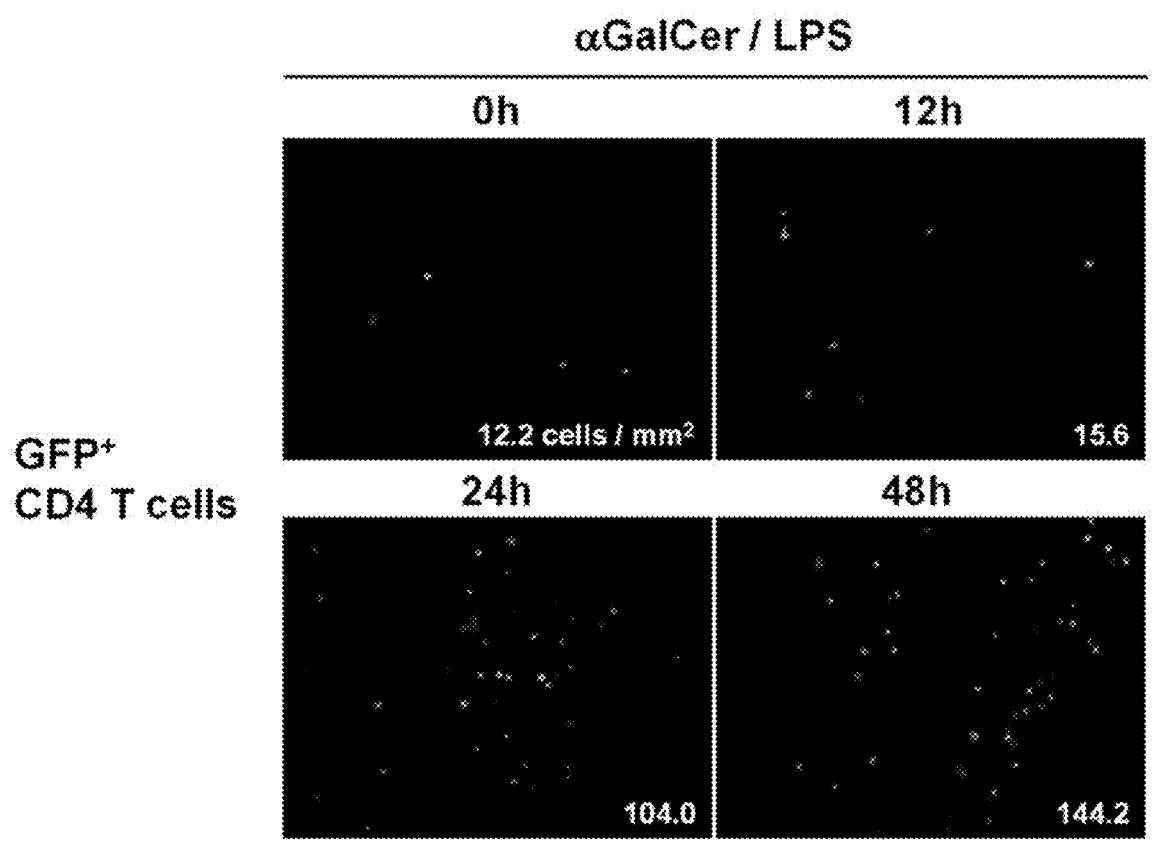
FIG. 2D are photographs for showing the results of temporal measurement of CD4 T cell infiltration into the lungs in the mouse FARDS model. Infiltration of GFP-positive CD4 T cells (GFP+ CD4 T cells) into the lungs was found in about 24 hours after LPS administration (Example 2).

In the mice administered αGalCel and LPS, accumulation of GFP-positive CD4 T cells in the lungs was found from after about 24 hours after the administration of LPS (FIG. 2D). It was revealed that the accumulation of CD4 T cells in the lungs was found later than the accumulation of neutrophils in the lungs.

EXAMPLE 3

Infiltration of immune inflammatory cells in the lungs and CD69 expression in the infiltrating immune cells were investigated in a mouse FARDS model. The mouse FARDS model generated by the same method as in Example 1 was used.

After 3 days from the LPS administration, alveolar lavage (bronchoalveolar lavage: BAL) was performed in accordance with a previous report (Non Patent Literature 19). All alveolar lavage fluid was collected, and cells in 150 μl aliquots were counted. For 100,000 living BAL cells, cell types and CD69 expressions were investigated by flow cytometry. The number of each type of cells per lungs of one mouse was calculated from the total cell number and the percentage of each cell type according to flow cytometry.

Figure 3A:
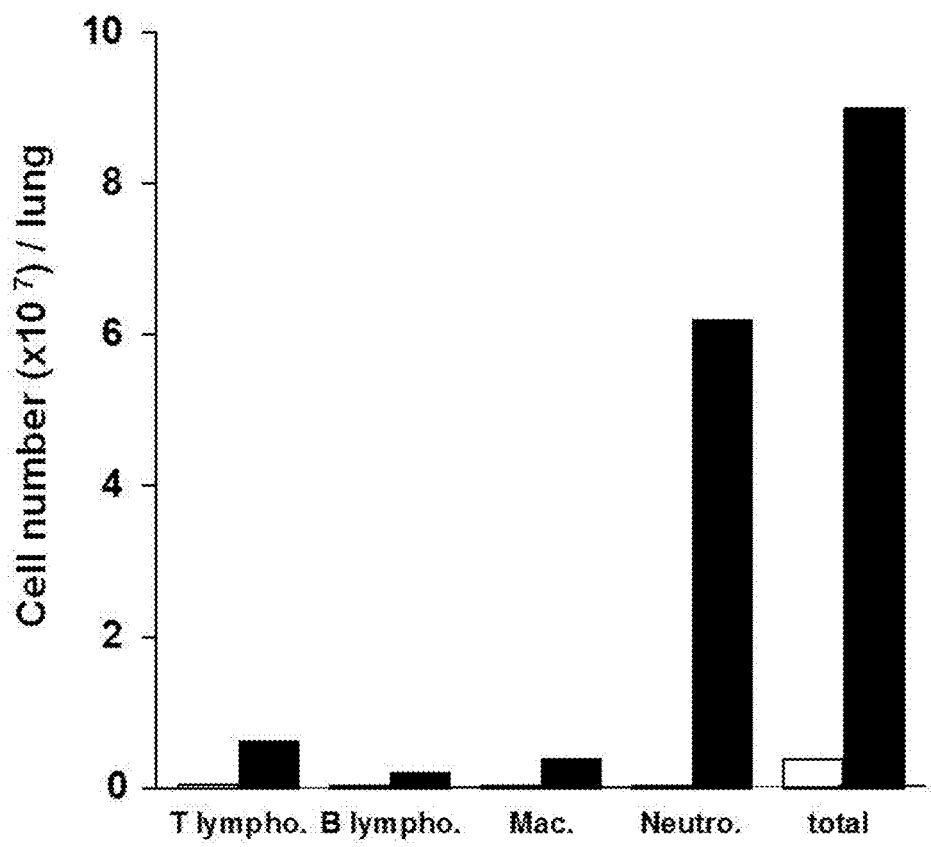
FIG. 3A is a graph for showing the results of measurement of the types and the numbers of immune inflammatory cells in alveolar lavage fluid thereof in the mouse FARDS model. In the mouse FARDS model (black bars), increases in immune inflammatory cell infiltration into the lungs were found as compared to mice administered only PBS and not developing FARDS (white bars). The vertical axis of the graph represents the number of cells of each type per lung (Cell number ($\times 10^7$)/lung).
Figure 3B:
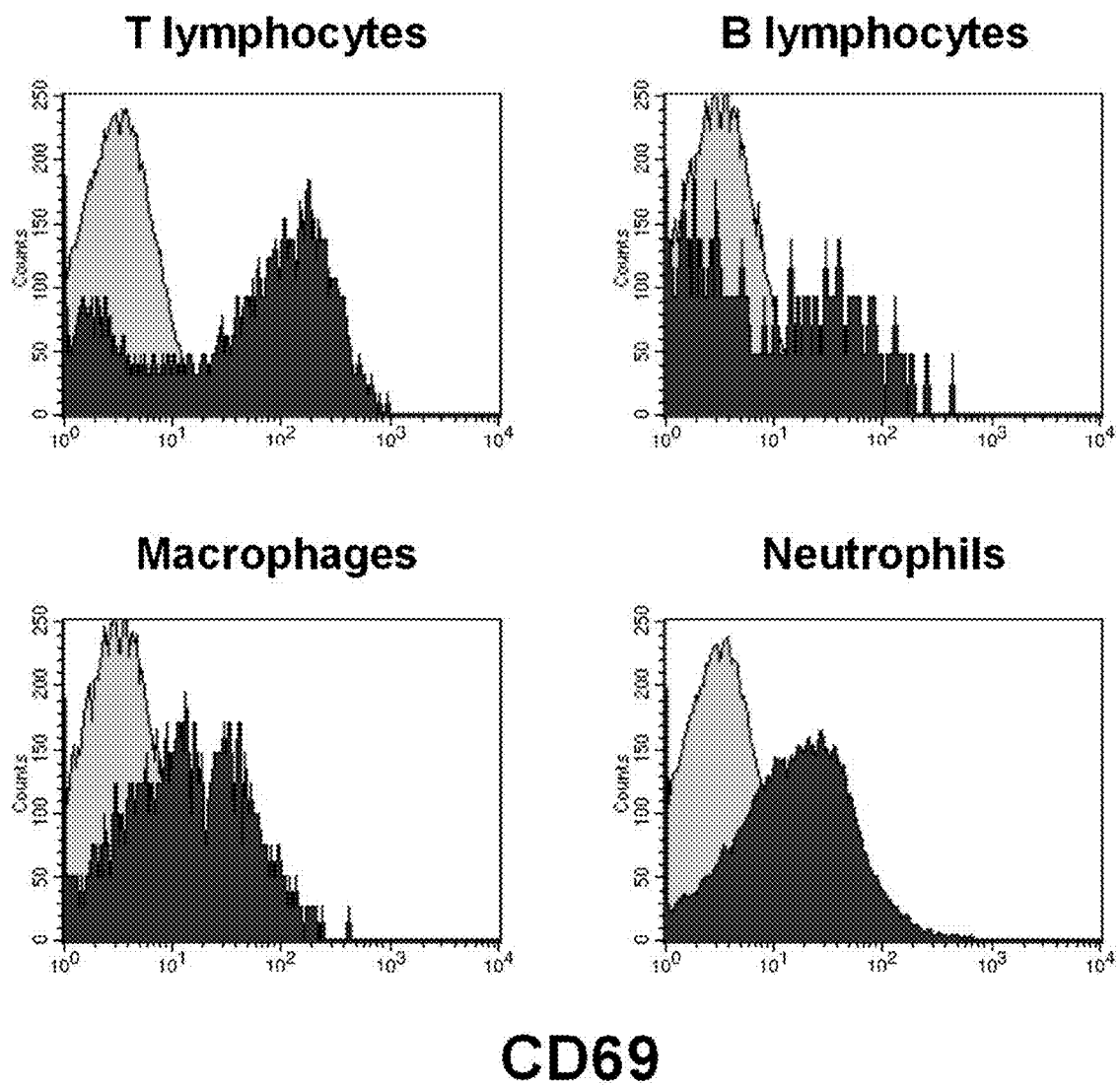
FIG. 3B are graphs for showing the results of an investigation of CD69 molecule expression of cells that have infiltrated the lungs in the mouse FARDS model. In each of T lymphocytes, B lymphocytes, macrophages, and neutrophils that have infiltrated the lungs, a remarkable increase in CD69 expression was found. The vertical axis of each of the graphs represents the number of cells (Counts), and the horizontal axis represents the expression level of the CD69 molecule (Example 3).

Infiltration of immune inflammatory cells into the lungs was dramatically increased after LPS administration in the mouse FARDS model (FIG. 3A). In particular, the accumulation of neutrophils was characteristically found. In addition, an increase in CD69 expression was observed in each of the infiltrating T lymphocytes, B lymphocytes, macrophages, and neutrophils (FIG. 3B).

EXAMPLE 4

From the investigation results of Example 3, increases in CD69 expression were observed in the infiltrating immune inflammatory cells in the lungs of the mouse FARDS model. In view of this, the effect of anti-CD69 antibody administration on neutrophil infiltration into the lungs was investigated in the mouse FARDS model.

A mouse FARDS model generated by the same method as in Example 2 was used. After 24 hours from the cell transfusion (Day −2), anti-CD69 mAb (H1.2F3; Armenian hamster IgG; manufactured by Affymetrix) was intraperitoneally (i.p.) injected at a dose of 200 μg/mouse, αGalCel was transnasally administered after 24 hours (Day −1), and LPS was transnasally administered after further 24 hours (Day 0) to induce fulminant acute pneumonia. After 24 hours from the LPS administration, the lungs of the mice were removed, and GFP-positive neutrophils were observed using a fluorescence microscope (M205FAA, manufactured by Nikon Corporation).

The anti-CD69 antibody H1.2F3 used in this Example has been confirmed to be available for detecting CD69 expression by flow cytometry, when the antibody is fluorescently labeled and applied for direct staining of live cells of mice. In the direct staining of living cells, antibody molecules cannot enter the cells. Therefore, successful detection of CD69 by flow cytometer means that the used anti-CD69 antibody recognizes and binds to an extracellular region of a CD69 molecule.

Figure 4:
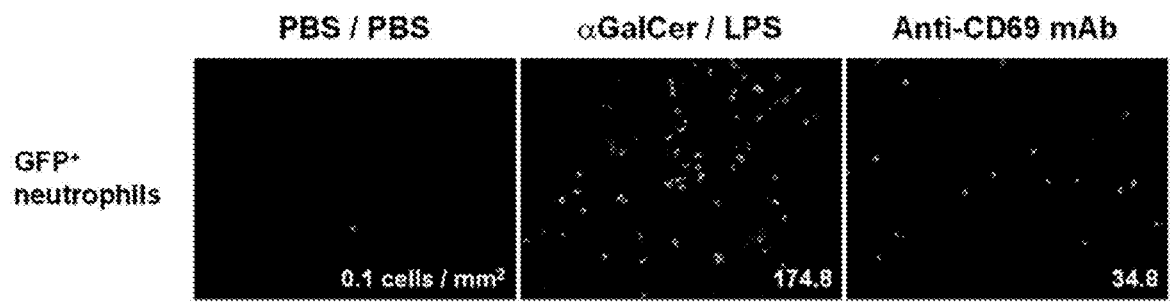
FIG. 4 are photographs for showing that remarkable infiltration of GFP-positive neutrophils (GFP+ neutrophils) into the lungs found after FARDS induction in the mouse FARDS model was suppressed by pre-administering an anti-CD69 antibody (Anti-CD69 mAb).

In the mice administered αGalCel and LPS, remarkable infiltration of GFP-positive neutrophils into the lungs was observed, but the neutrophil infiltration into the lungs was suppressed by administering the anti-CD69 antibody before the development of the disease (FIG. 4). In addition, the formation of an aggregate by the neutrophils infiltrating the lungs was suppressed by administering the anti-CD69 antibody before the development of the disease.

The above-mentioned results suggest that the anti-CD69 antibody can be used for suppressing neutrophil infiltration into the lungs and the formation of an aggregate of infiltrating neutrophils.

EXAMPLE 5

Figure 5A:
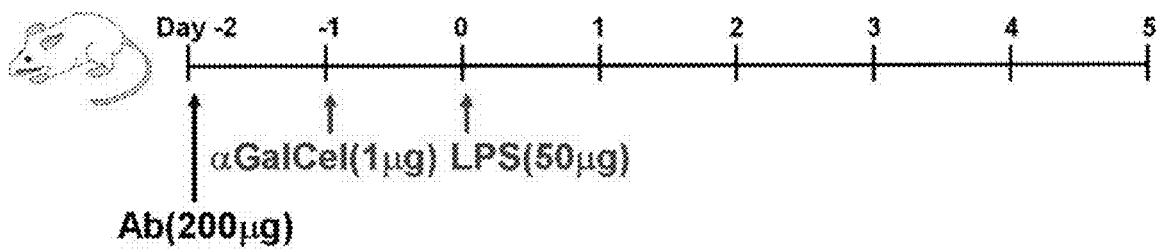
FIG. 5A is a diagram for describing a drug administration procedure for investigating the effect of pre-administration of the anti-CD69 antibody in the mouse FARDS model. The anti-CD69 antibody was administered to wild-type mice (Day −2), αGalCel was transnasally administered thereto 24 hours after that (Day −1), and further, LPS was transnasally administered thereto 24 hours after that (Day 0).

The suppressive effect of anti-CD69 antibody administration before the development of FARDS on fulminant acute pneumonia was investigated. A mouse FARDS model generated by the same method as in Example 1 was used. 24 hours before αGalCel administration (Day −2), anti-CD69 mAb (H1.2F3) was intraperitoneally (i.p.) administered at a dose of 200 μg (FIG. 5A). As a negative control, similar treatment was performed using an Armenian hamster IgG isotype control antibody (manufactured by BioLegent; hereinafter referred to as control antibody).

After the LPS administration, the mice were each confirmed to be dead or alive every 12 hours to calculate the survival rate. After 48 hours from the LPS administration, arterial blood was collected from each of the mice, and was measured for an arterial oxygen partial pressure using an automatic analyzer (ABS555, Radiometer Copenhagen, Denmark) to calculate the P/F ratio. For histological analysis, a lung obtained from each of the mice after 72 hours from the LPS administration was fixed in 4% paraformaldehyde and embedded in paraffin to prepare a section, which was subjected to H&E staining for histological examination. The sample was examined under an optical microscope.

1. Mortality Rate in Mouse FARDS Model

Figure 5B:
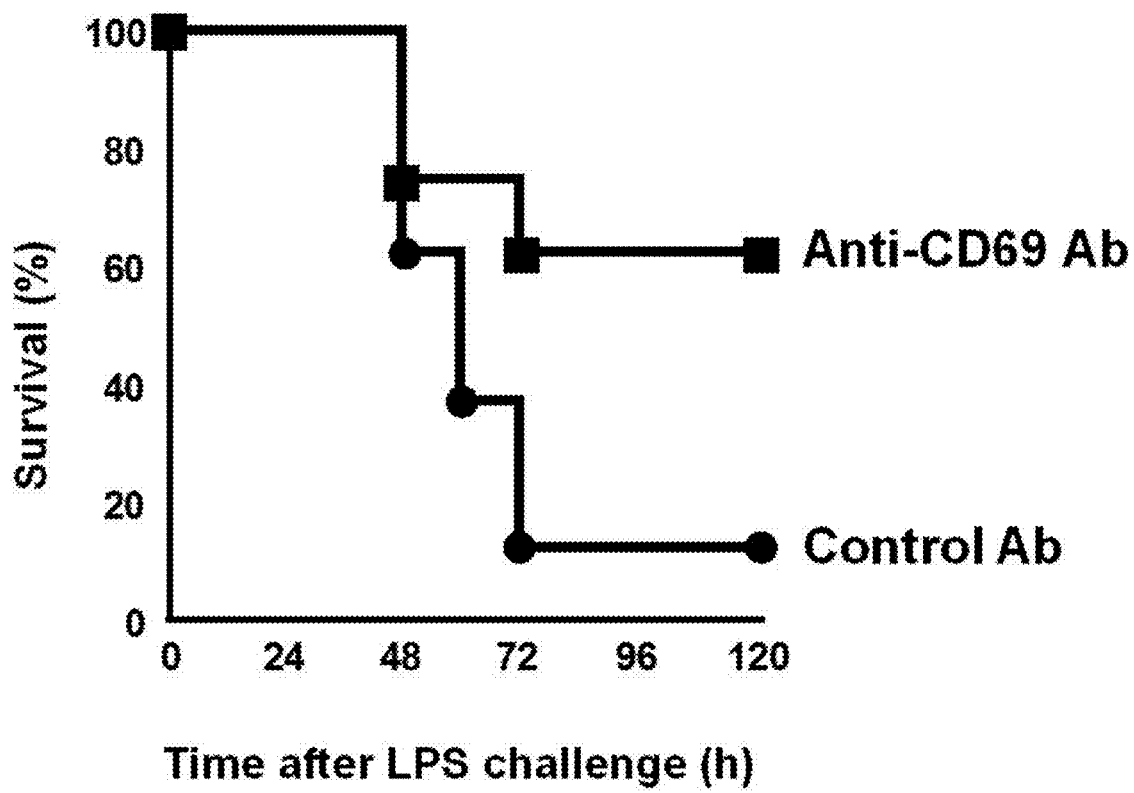
FIG. 5B is a graph for showing the results of a temporal investigation of the effect of pre-administration of the anti-CD69 antibody on the survival rate of the mouse FARDS model after LPS administration. As a result of the administration of the anti-CD69 antibody (Anti-CD69 Ab) before the administration of αGalCer, the survival rate was remarkably increased as compared to that in the case where a control antibody (Control Ab) was administered. The vertical axis of the graph represents survival rate (Survival (%)), and the horizontal axis represents time after LPS administration (Time after LPS challenge (h)) (Example 5).

The investigation was performed using eight FARDS model mice, and as a result, a remarkable decrease in mortality rate was observed when the anti-CD69 antibody was administered before the development of FARDS (FIG. 5B). Specifically, 60% or more of the mice escaped death and survived.

2. Lung Findings in Mouse FARDS Model

Figure 5C:
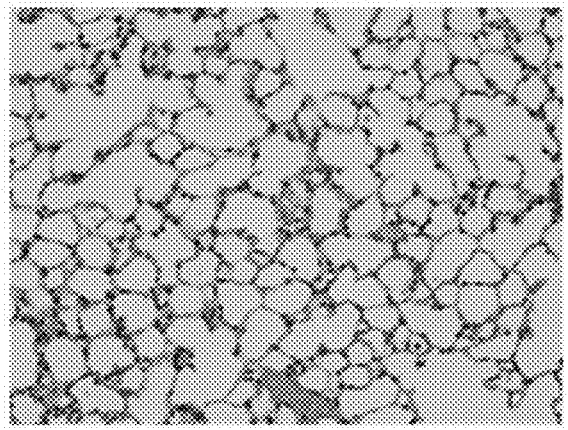
FIG. 5C are photographs for showing that remarkable neutrophil infiltration into the lungs found in the mouse FARDS model was decreased by administering the anti-CD69 antibody (Anti-CD69 mAb) before the administration of αGalCer.
Figure 5C:
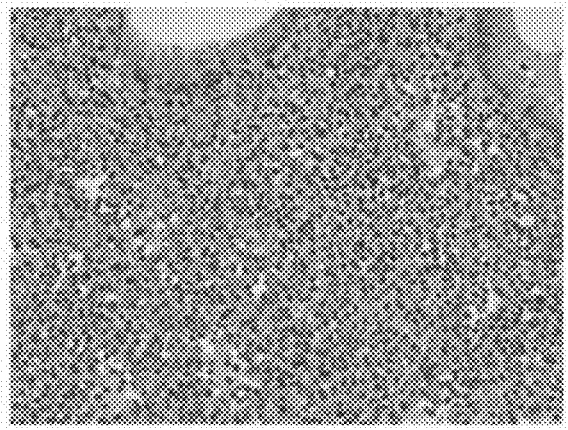
Figure 5C:
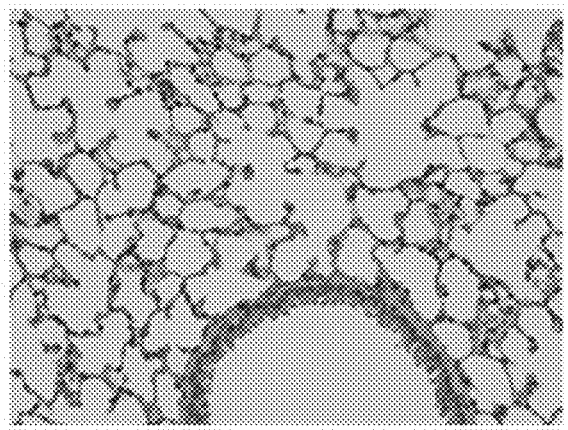
Figure 5C:
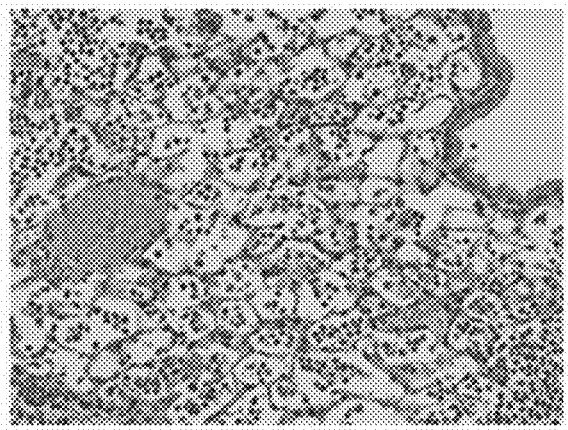

In histopathological images taken 72 hours after the administration of LPS, intense inflammatory cell infiltration was observed in the lung tissue of the mice administered the control antibody, but in the lung tissue of the mice administered the anti-CD69 antibody before the development of FARDS, infiltration of inflammatory cells was suppressed, and the degree of inflammation was relieved (FIG. 5C).

3. P/F Ratio in Mouse FARDS Model

Figure 5D:
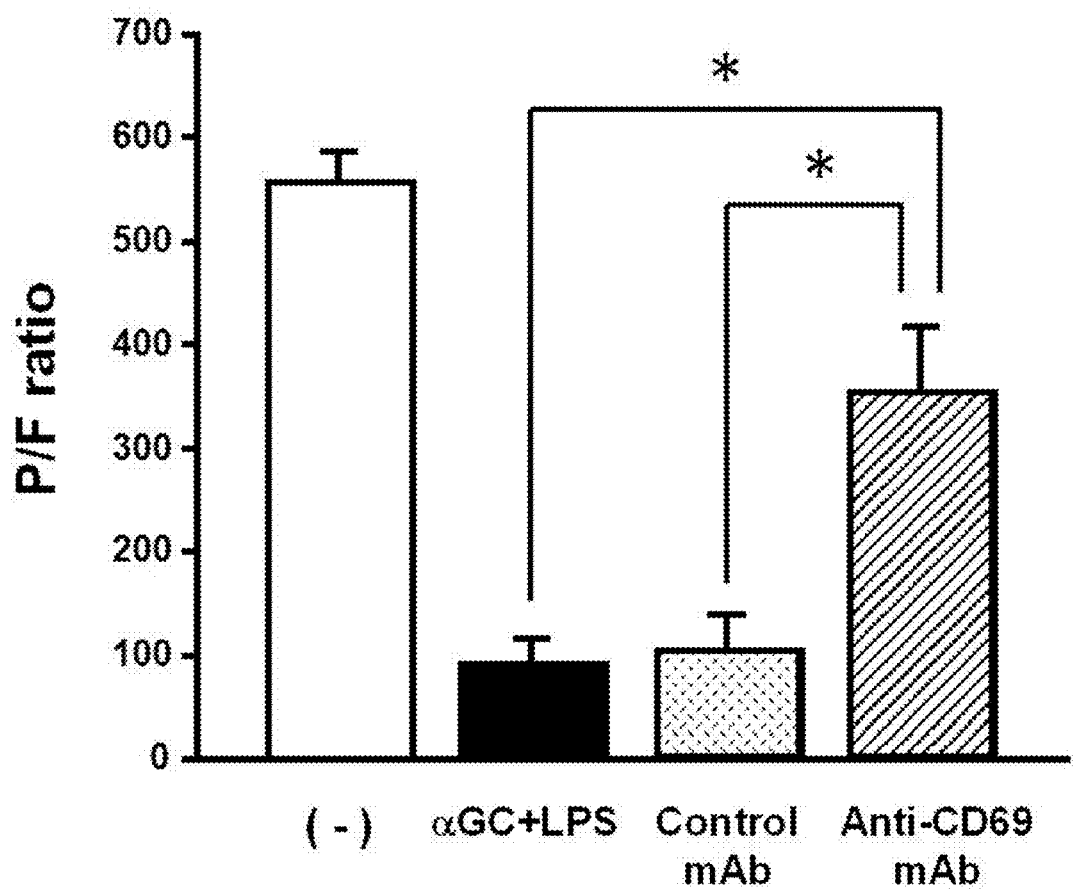
FIG. 5D is a graph for showing that the low P/F ratio found in the mouse FARDS model was significantly improved by administering the anti-CD69 antibody (Anti-CD69 mAb) before the administration of αGalCer.

The P/F ratio was 91.6±24.0 in the mouse FARDS model, whereas in the wild-type mice administered only PBS (hereinafter referred to as wild-type mice in a steady state), the P/F ratio was 559.0±25.5. In the mice administered the anti-CD69 antibody before the development of FARDS, the P/F ratio was improved to 353.9±62.3. Meanwhile, in the mice administered the control antibody before the development of FARDS, the P/F ratio was 105.0±33.7, and no improvement was found. These results revealed that the decrease in P/F ratio found in the mouse FARDS model was remarkably improved by administering the anti-CD69 antibody before the development of FARDS (FIG. 5D).

It was revealed that the anti-CD69 antibody, when administered before FARDS induction, increased the survival rate of the mice after the development of FARDS, suppressed the infiltration of inflammatory cells into the lungs, and remarkably improved the P/F ratio.

EXAMPLE 6

Figure 6A:
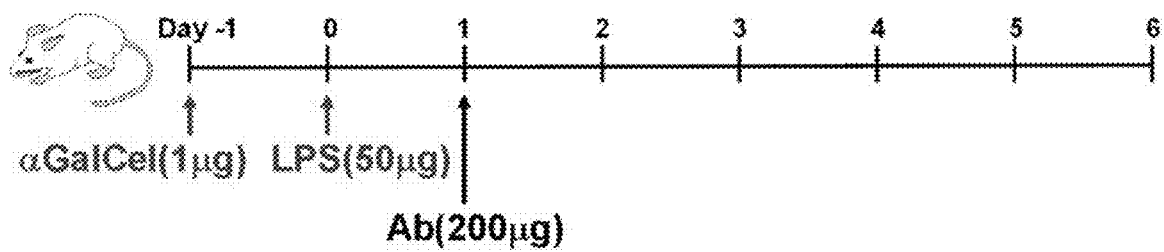
FIG. 6A is a diagram for describing a drug administration procedure for investigating the effect of anti-CD69 antibody administration after FARDS induction in the mouse FARDS model. αGalCel was transnasally administered to wild-type mice (Day −1), LPS was transnasally administered thereto 24 hours after that (Day 0) to induce FARDS, and the anti-CD69 antibody was administered thereto 24 hours after the LPS administration (Day 1).

The suppressive effect of anti-CD69 antibody administration after the development of FARDS on fulminant acute pneumonia was investigated. The mouse FARDS model generated by the same method as in Example 1 was used. After 24 hours from LPS administration, anti-CD69 mAb (H1.2F3; Armenian hamster IgG; manufactured by Affymetrix) was intraperitoneally (i.p.) administered at a dose of 200 μg (FIG. 6A). As a negative control, similar treatment was performed using the control antibody.

After the LPS administration, the mice were each confirmed to be dead or alive every 12 hours to calculate the survival rate. For histological analysis, a lung obtained from each of the mice after 72 hours from the LPS administration was fixed in 4% paraformaldehyde and embedded in paraffin to prepare a section, which was subjected to H&E staining for histological examination. The sample was examined under an optical microscope.

1. Mortality Rate in Mouse FARDS Model

Figure 6B:
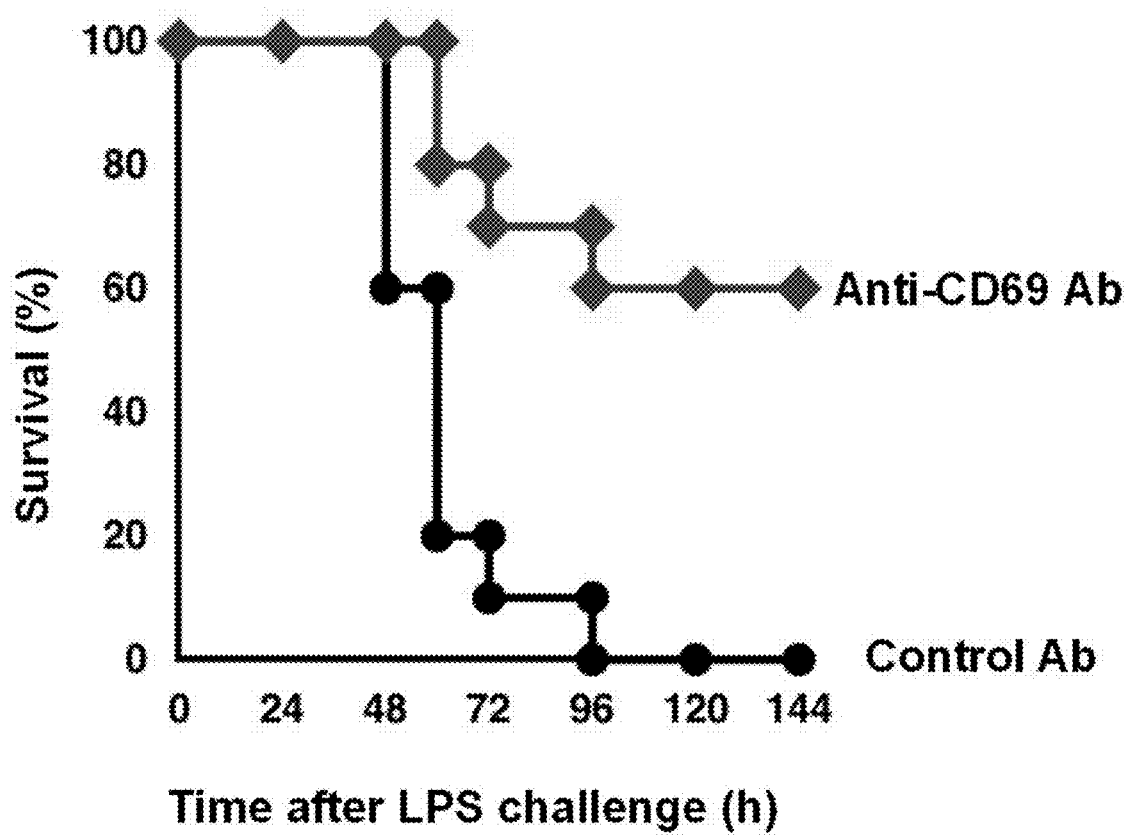
FIG. 6B is a graph for showing the results of a temporal investigation of the effect of anti-CD69 antibody administration after the administration of LPS on the survival rate of the mouse FARDS model. As a result of the administration of the anti-CD69 antibody (Anti-CD69 Ab) after the administration of LPS, the survival rate was remarkably increased as compared to that in the case where the control antibody (Control Ab) was administered. The vertical axis of the graph represents survival rate (Survival (%)), and the horizontal axis represents time after LPS administration (Time after LPS challenge (h)) (Example 6).

An investigation was performed using ten FARDS model mice, and as a result, a remarkable decrease in mortality rate was observed when the anti-CD69 antibody was administered after the development of FARDS (FIG. 6B). Specifically, 60% or more of the mice escaped death and survived.

2. Lung Findings in Mouse FARDS Model

Figure 6C:
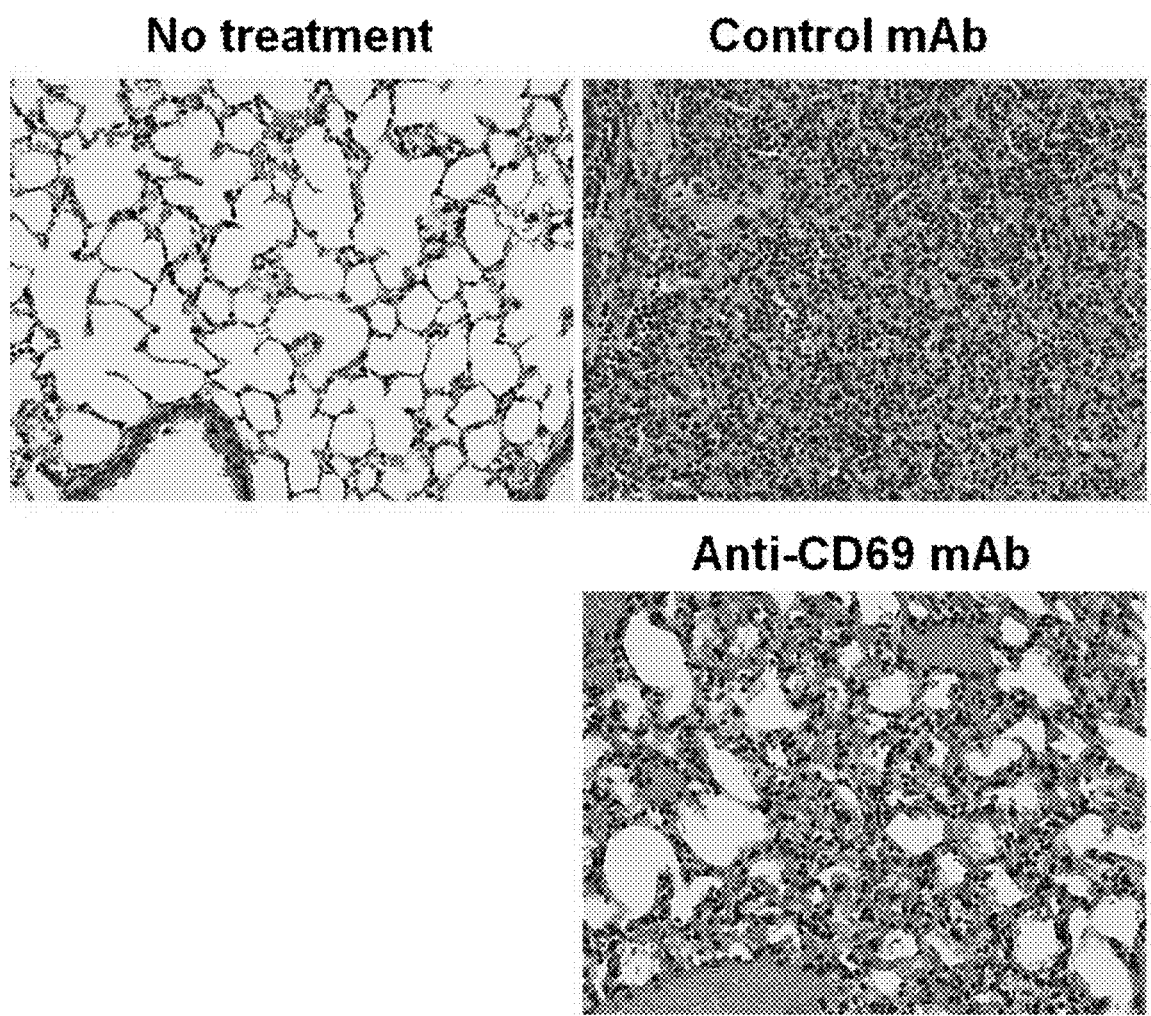
FIG. 6C are photographs for showing that remarkable neutrophil infiltration into the lungs found in the mouse FARDS model was decreased by administering the anti-CD69 antibody (Anti-CD69 mAb) after the administration of LPS.

In histopathological images taken 72 hours after the administration of LPS, intense inflammatory cell infiltration was observed in the lung tissue of the mice administered the control antibody, but in the lung tissue of the mice administered the anti-CD69 antibody after the development of FARDS, infiltration of inflammatory cells was suppressed (FIG. 6C). As compared to the lung tissue of the mice administered the anti-CD69 antibody before the development of FARDS, the degree of cell infiltration suppression was small, but clearly different from the control antibody administration group, there remained a space allowing gas exchange in the lung tissue. Accordingly, the survival rate increased.

Thus, it was revealed that the anti-CD69 antibody gave a comparable survival rate even by administration after FARDS induction to that in the case of administration before the induction, and suppressed the infiltration of inflammatory cells into the lungs.

EXAMPLE 7

The involvement of CD69 expression of neutrophils in neutrophil accumulation in the lungs of the mouse FARDS model was investigated.

Individuals obtained by crossing CD69 knockout mice (CD69KO) obtained by backcrossing CD69-deficient mice (Non Patent Literature 1) with C57BL/6 mice 15 or more times with GFP transgenic mice (C57BL/6 background), and red fluorescent protein (RFP) transgenic mice (C57BL/6 background) (Non Patent Literature 20) were used. Neutrophils were purified from the femur bone marrow of those mice using an AutoMACS sorter (Miltenyi Biotec) to a purity of 98%. 2,000,000 each of the two kinds of isolated neutrophils, namely CD69KO-GFP-positive neutrophils and RFP-positive neutrophils were intravenously injected into an identical wild-type C57BL/6 mice (Day −3). After 48 hours from the cell transfusion (Day −1), αGalCel was transnasally administered to the C57BL/6 mice at a dose of 1 μg/50 μl PBS/mouse, and 24 hours after that (Day 0), LPS was transnasally administered thereto at a dose of 50 μg/50 μl PBS/mouse to induce fulminant acute pneumonia. After 24 hours from the LPS administration, the lungs of the mice were removed, and GFP-positive and RFP-positive neutrophils were observed using a fluorescence microscope (M205FA, manufactured by Nikon Corporation).

Figure 7:
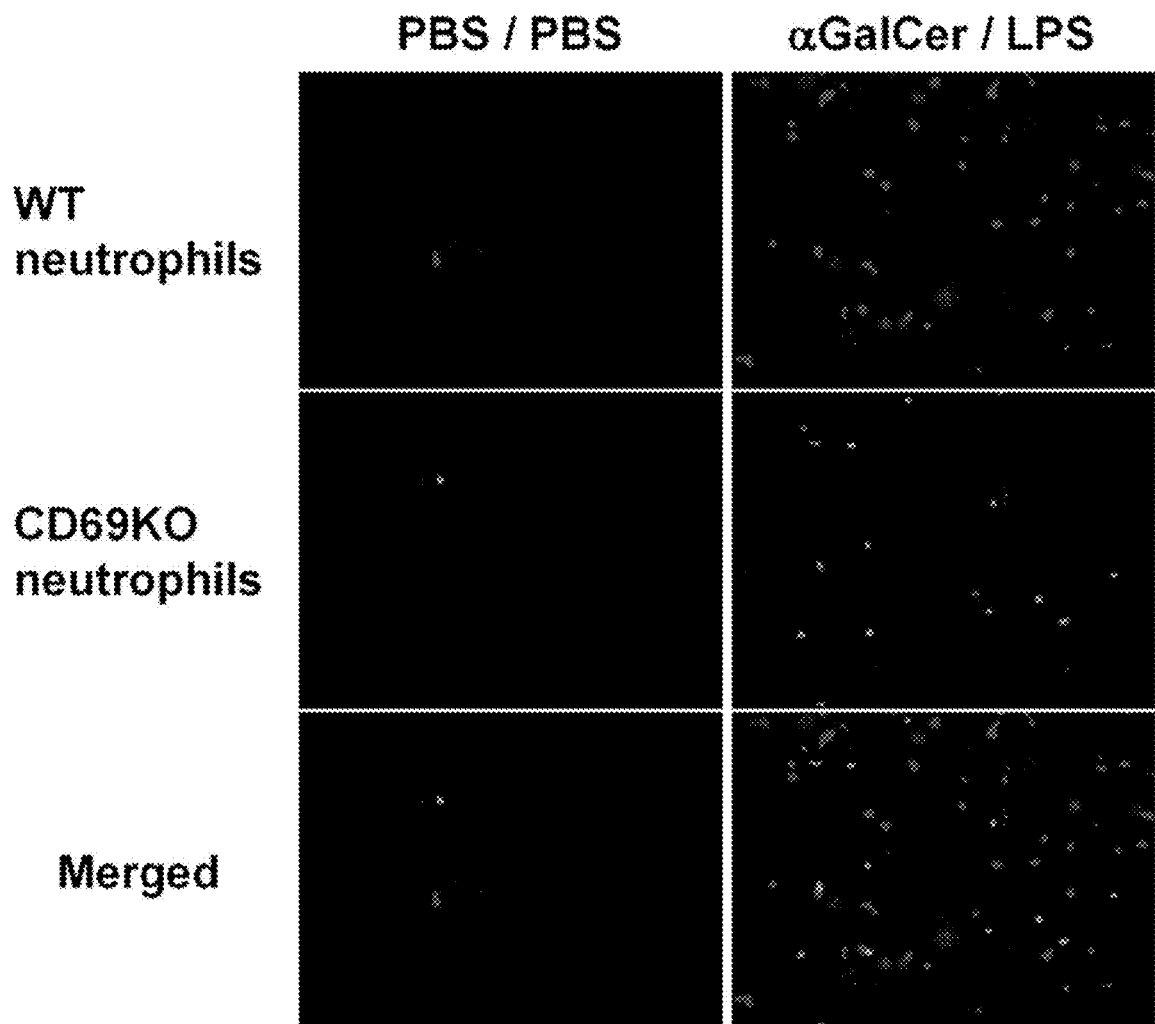
FIG. 7 are photographs for showing that CD69-deficient mouse-derived neutrophils had a low degree of infiltration into the lungs in the mouse FARDS model.

In the lung tissue of the FARDS-induced mice, intense infiltration of RFP transgenic mouse-derived RFP-positive neutrophils (indicated by WT neutrophil in FIG. 7) was observed (FIG. 7). In contrast, the degree of infiltration of CD69 knockout mouse-derived GFP-positive neutrophils (indicated by CD69KO neutrophil in FIG. 7) into the lung tissue was remarkably low.

Thus, it was revealed that neutrophils not expressing CD69 hardly infiltrated the lungs. The results suggested the possibility of CD69 being involved in the kinetics of neutrophils in the body.

The results of Examples described above suggested that the CD69 molecule can serve as a satisfactory therapeutic target molecule for FARDS, which is a refractory inflammatory disease. The treatment of FARDS becomes possible through the suppression of the expression or function of CD69 in immune inflammatory cells, for example, neutrophils.

INDUSTRIAL APPLICABILITY

The present invention provides the pharmaceutical composition for preventing and/or treating fulminant acute pneumonia containing the CD69 antagonist, such as the anti-CD69 antibody, and the method of preventing and/or treating fulminant acute pneumonia, and is applicable in a pharmaceutical field.

The invention claimed is:

1. A method of treating fulminant acute pneumonia in a subject, comprising administering an effective amount of a CD69 antagonist to the subject, wherein the CD69 antagonist is administered to the subject after the subject has developed the fulminant acute pneumonia, the subject has not received administration of the CD69 antagonist before the development of the fulminant acute pneumonia, and the CD69 antagonist is an antibody that specifically recognizes CD69.

2. The method according to claim 1, wherein the antibody specifically recognizes extracellular region of CD69.

3. The method according to claim 1, wherein the antibody has an antagonistic action against CD69.

4. The method according to claim 1, wherein the subject is diagnosed to be in need of treatment of fulminant acute pneumonia, and the CD69 antagonist is administered to the subject at an effective dose for the treatment of fulminant acute pneumonia.

5. The method according to claim 1, wherein the subject is diagnosed to be in need of suppression of intra-alveolar neutrophil aggregation, and the CD69 antagonist is administered to the subject at an effective dose for the suppression.

6. The method according to claim 1, wherein the subject is diagnosed to be in need of suppression of pulmonary neutrophil infiltration, and the CD69 antagonist is administered to the subject at an effective dose for the suppression.

* * * * *